(12) United States Patent
Betzer et al.

(10) Patent No.: US 10,059,908 B2
(45) Date of Patent: Aug. 28, 2018

(54) USE OF LACTONES AS ODOR MASKING AGENTS

(71) Applicants: Marcus Betzer, Holzminden (DE); Hans-Georg Reindl, Holzminden (DE); Nicole Schulze, Freden (DE)

(72) Inventors: Marcus Betzer, Holzminden (DE); Hans-Georg Reindl, Holzminden (DE); Nicole Schulze, Freden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 15/031,970

(22) PCT Filed: Oct. 25, 2014

(86) PCT No.: PCT/EP2014/072927
§ 371 (c)(1),
(2) Date: Apr. 25, 2016

(87) PCT Pub. No.: WO2015/062997
PCT Pub. Date: May 7, 2015

(65) Prior Publication Data
US 2016/0272921 A1    Sep. 22, 2016

(30) Foreign Application Priority Data
Oct. 28, 2013 (EP) .................................. 13190502

(51) Int. Cl.
| | | |
|---|---|---|
| *C11D 3/00* | (2006.01) | |
| *C11B 9/00* | (2006.01) | |
| *A61Q 13/00* | (2006.01) | |
| *A61L 9/01* | (2006.01) | |
| *C11D 3/20* | (2006.01) | |
| *A61K 8/49* | (2006.01) | |
| *A61Q 19/00* | (2006.01) | |

(52) U.S. Cl.
CPC ............ *C11B 9/0076* (2013.01); *A61K 8/498* (2013.01); *A61K 8/4973* (2013.01); *A61L 9/01* (2013.01); *A61Q 19/00* (2013.01); *C11B 9/008* (2013.01); *C11D 3/0068* (2013.01); *C11D 3/2096* (2013.01); *A61K 2800/10* (2013.01); *A61Q 13/00* (2013.01)

(58) Field of Classification Search
CPC ..... C11B 9/0073; C11B 9/0076; C11B 9/008; A61L 9/01; A61Q 13/00; C11D 3/0068
See application file for complete search history.

(56) References Cited

U.S. PATENT DOCUMENTS

| | | | | |
|---|---|---|---|---|
| 5,540,853 | A | * | 7/1996 | Trinh ....................... A61K 8/02 510/101 |
| 2002/0197287 | A1 | | 12/2002 | Streit et al. |
| 2006/0207037 | A1 | | 9/2006 | Fadel et al. |
| 2007/0287659 | A1 | * | 12/2007 | Perring ................... A61K 8/35 512/5 |
| 2011/0293538 | A1 | * | 12/2011 | Ley ..................... A23L 1/22075 424/49 |

FOREIGN PATENT DOCUMENTS

| | | | |
|---|---|---|---|
| EP | 2 386 211 A1 | | 11/2011 |
| JP | 2004018431 A | * | 1/2004 |
| WO | 96/04940 A1 | | 2/1996 |
| WO | 03/070871 A1 | | 8/2003 |
| WO | 2004/009750 A1 | | 1/2004 |

OTHER PUBLICATIONS

English-language machine translation of JP-2004018431-A (retrieved from J-PlatPat, Feb. 2018). (Year: 2018).*
CAPLUS Abstract of JP-2004018431-A (retrieved from STN, Feb. 2018). (Year: 2018).*

* cited by examiner

*Primary Examiner* — Theodore R. West
(74) *Attorney, Agent, or Firm* — Dilworth & Barrese, LLP

(57) ABSTRACT

Suggested is a method for masking odoriferous incorrect notes in oleochemical preparations, by adding to said compositions specific lactones.

4 Claims, No Drawings

USE OF LACTONES AS ODOR MASKING AGENTS

FIELD OF INVENTION

The invention is in the field of oleochemical products and relates to the use of specific lactones for odour improvement.

STATE OF THE ART

Oleochemical raw materials, such as fats and oils, and derivatives thereof of the first and second order are important starting materials for producing both laundry detergents, dishwashing detergents and cleaners, but also cosmetic products. The triglycerides and the fatty acid esters obtained therefrom by transesterification serve for example as oil bodies, the derivatives produced by saponification or hydrogenation giving anionic and nonionic surfactants, such as e.g. soaps, fatty alcohol sulphates, fatty alcohol ether sulphates or fatty alcohol polyglycol ethers. A common feature of all of these substances is that they have a typical greasy odour which, upon prolonged storage, moreover develops further unpleasant notes. Reasons for this are, alongside short-chain free fatty acids which are released by saponification of the triglycerides, in particular aldehydes and other substances which are formed by oxidation. As a rule, the odour quality of the oleochemical substances is inadequate in order to use them directly in the various end products.

One method of solving this problem consists in subjecting batches that are not perfect in terms of odour to a post-treatment, so-called deodorization. Here, the raw materials are treated with hot steam, whereupon the odour carriers are distilled off to a large extent. However, the process is associated with a high input of energy. Particularly when it is a question of processing fats and oils that are as cost effective as possible, which by their very nature have the highest proportion of said undesired odour carriers, this measure is in economical terms naturally counterproductive.

In many cases, it is also possible to confine the unpleasant odour by adding an encapsulation agent, as is described for example in WO 2009 131748 A1 (BELLE AIR). However, this measure can also be barely realised from an economical point of view.

From the state of the art compositions, in particular cosmetic preparations are known comprising one or two $C_8$-$C_{12}$ alkyllactones (WO 2003 070871 A1, US 2006 0207037 A1, WO 2004 009750 A1, WO 19960 04940 A1, US 2002 0197287 A1). None of these references, however, disclose the use of said lactones for masking unpleasant odours.

The most common alternative hitherto has consisted in adding fragrances to the raw materials that are not perfect in terms of odour—or to the end products confectioned therewith-, said fragrances concealing (masking) the unpleasant odour or combining with it in such a way that a new odour is formed which is less unpleasant. This process too is complex and expensive since hitherto considerable amounts of such masking substances have always been required.

The object of the present invention therefore consisted in providing new active ingredients which are able, even in very small concentrations, to counteract the unpleasant scent notes arising in oleochemical raw materials and in the end products produced therewith, such as, for example, greasy or rancid odour, i.e. to conceal them or combine with them such that a new pleasant, for example sweet, creamy or aromatic odour is formed.

DESCRIPTION OF THE INVENTION

The invention provides a method for masking odoriferous incorrect notes in oleochemical preparations by adding lactones of the formula (Ia) or (Ib)

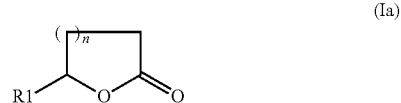

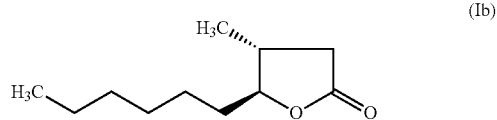

in which $R^1$ is a linear or branched, saturated or unsaturated, optionally hydroxy-substituted hydrocarbon radical having 2 to 22 carbon atoms and 0 or 1 to 3 double bonds and n is the number 1 or 2, Surprisingly, it has been found that the lactones of the formula (I), even in small amounts, are able not only to mask unpleasant odours in a large number of oleochemical formulations which have in particular greasy or rancid notes, but to even intensify pleasant odour notes and to bring them to the fore.

Lactones

The alkyl lactones of the present invention are known substances which can be obtained by the relevant processes of organic chemistry. A simple method for producing 5-membered γ-lactones consists in evaporating aqueous solutions of corresponding hydroxycarboxylic acids. Another method of preparing lactones is the Baeyer-Villinger oxidation, during which cyclic ketones are oxidized with peroxycarboxylic acids with ring expansion.

In the context of the invention, the lactones that are particularly readily suitable for improving the odour note of oleochemical compositions are those in which, in formula (I), $R^1$ is linear alkyl radicals having 2 to 14 and in particular 6 to 12 carbon atoms.

The lactones here serve specifically for the masking of odour notes which are caused by free fatty acids, aldehydes, and oxidation products of fats and oils in oleochemical products.

In the context of the present invention, the lactones can be used in any desired products where it is a case of masking unpleasant odour notes that are caused primarily by fatty derivatives, and/or of replacing them by pleasant odour perceptions. Typical examples of product groups in which the lactones can be used are, for example, soap bases, laundry detergents, dishwashing detergents and cleaners, and also cosmetic preparations. Preferably, the lactones are used in amounts of from 0.01 to 1% by weight, in particular 0.02 to 0.5% by weight and particularly preferably 0.05 to 0.1% by weight—based on the preparations.

Laundry Detergents, Dishwashing Detergents and Cleaners

The invention further provides laundry detergents, dishwashing detergents and cleaners at least four lactones selected from the group consisting of γ-hexalactone, γ-heptalactone, γ-octalactone, γ-nonalactone, γ-decalactone, γ-undecalactone, γ-dodecalactone, δ-hexalactone, δ-heptalactone, δ-octalactone, δ-nonalactone, δ-decalactone, δ-undecalactone, δ-dodecalactone, and mixtures thereof, where the use concentration of the lactone or of the lactones is usually in the range from 0.01 to 1% by weight, preferably 0.1 to 0.5% by weight—based on the preparations.

The laundry detergents, dishwashing detergents and cleaners are preferably in liquid form and can have further standard commercial constituents, such as, for example, surfactants, builders, bleaches, bleach activators, thickeners, enzymes, electrolytes, pH regulators, dyes and fragrances, foam inhibitors, antiredeposition agents, optical brighteners, greying inhibitors, anticrease agents, antimicrobial active ingredients, preservatives, antioxidants, antistats, UV adsorbers, heavy metal complexing agents and the like. These auxiliaries are described in more detail below:

Surfactants

Surfactants that can be used to produce the laundry detergents or cleaners are, besides the nonionic surfactants, also anionic, cationic, amphoteric and/or nonionic surfactants and branched alkyl sulphates.

Nonionic surfactants used are preferably alkoxylated, advantageously ethoxylated, in particular primary alcohols having preferably 8 to 18 carbon atoms and on average 1 to 12 mol of ethylene oxide (EO) per mole of alcohol, in which the alcohol radical can be linear or preferably 2-methyl-branched, and/or can contain linear and methyl-branched radicals in a mixture, as are customarily present in oxo alcohol radicals. In particular, however, preference is given to alcohol ethoxylates with linear radicals from alcohols of native origin having 12 to 18 carbon atoms, for example from coconut, palm, tallow fatty or oleyl alcohol, and on average 2 to 8 EO per mole of alcohol. The preferred ethoxylated alcohols include, for example, C12-14-alcohols with 3 EO, 4 EO or 7 EO, C9-11-alcohol with 7 EO, C13-15-alcohols with 3 EO, 5 EO, 7 EO or 8 EO, C12-18-alcohols with 3 EO, 5 EO or 7 EO and mixtures of these, such as mixtures of C12-14-alcohol with 3 EO and C12-18-alcohol with 7 EO. The stated degrees of ethoxylation are statistical average values which can be an integer or a fraction for a specific product. Preferred alcohol ethoxylates have a narrowed homologue distribution (narrow range ethoxylates, NRE). In addition to these nonionic surfactants, fatty alcohols with more than 12 EO can also be used. Examples thereof are tallow fatty alcohol with 14 EO, 25 EO, 30 EO or 40 EO. Nonionic surfactants which contain EO and PO groups together in the molecule can also be used according to the invention. In this connection it is possible to use block copolymers with EO-PO block units or PO-EO block units, but also EOPO-EO copolymers and PO-EO-PO copolymers. It is of course also possible to use mixed alkoxylated nonionic surfactants in which EO and PO units are not distributed blockwise, but randomly. Such products are obtainable as a result of the simultaneous action of ethylene oxide and propylene oxide on fatty alcohols.

A further class of nonionic surfactants which can be used advantageously for producing laundry detergents or cleaners are the alkyl polyglycosides (APG). Alkyl polyglycosides that can be used satisfy the general formula RO(G)Z, in which R is a linear or branched, in particular 2-methyl-branched, saturated or unsaturated, aliphatic radical having 8 to 22, preferably 12 to 18, carbon atoms, and G is the symbol which stands for a glycose unit having 5 or 6 carbon atoms, preferably glucose. The degree of glucosidation z here is between 1.0 and 4.0, preferably between 1.0 and 2.0 and in particular between 1.1 and 1.4.

Nonionic surfactants of the amine oxide type, for example N-cocoalkyl-N,N-dimethylamine oxide and N-tallow-alkyl-N,N-dihydroxyethylamine oxide, and the fatty acid alkanolamides may also be suitable for producing the detergents or cleaners. The amount of these nonionic surfactants is preferably not more than that of the ethoxylated fatty alcohols, in particular not more than half thereof.

Further suitable surfactants are polyhydroxy fatty acid amides of the formula

in which RCO is an aliphatic acyl radical having 6 to 22 carbon atoms, R1 is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride. The group of polyhydroxy fatty acid amides also includes compounds of the formula R—CO—N(R1-O—R2)-[Z], in which R is a linear or branched alkyl or alkenyl radical having 7 to 12 carbon atoms, R1 is a linear, branched or cyclic alkyl radical or an aryl radical having 2 to 8 carbon atoms, and R2 is a linear, branched or cyclic alkyl radical or an aryl radical or an oxyalkyl radical having 1 to 8 carbon atoms, where C1-4-alkyl or phenyl radicals are preferred and [Z] is a linear polyhydroxyalkyl radical whose alkyl chain is substituted with at least two hydroxyl groups, or alkoxylated, preferably ethoxylated or propoxylated derivatives of this radical. [Z] is preferably obtained by reductive amination of a sugar, for example glucose, fructose, maltose, lactose, galactose, mannose or xylose. The N-alkoxy- or N-aryloxy-substituted compounds can then be converted into the desired polyhydroxy fatty acid amides by reaction with fatty acid methyl esters in the presence of an alkoxide as catalyst.

The content of nonionic surfactants in the liquid detergents and cleaners is preferably 5 to 30% by weight, preferably 7 to 20% by weight and in particular 9 to 15% by weight, in each case based on the total composition.

Anionic surfactants used are, for example, those of the sulphonate and sulphate types. Suitable surfactants of the sulphonate type here are preferably C9-3-alkylbenzenesulphonates, olefinsulphonates, i.e. mixtures of alkene- and hydroxyalkanesulphonates, and also disulphonates, as are obtainable for example from C12-8-monoolefins with terminal or internal double bond by sulphonation with gaseous sulphur trioxide and subsequent alkaline or acidic hydrolysis of the sulphonation products. Also of suitability are alkane sulphonates which are obtained from C12-8-alkanes, for example by sulphochlorination or sulphoxidation with subsequent hydrolysis or neutralization. Likewise of suitability are also the esters of alpha-sulpho fatty acids (ester sulphonates), for example the alphasulphonated methyl esters of hydrogenated coconut, palm kernel or tallow fatty acids.

Also of suitability are sulphonation products of unsaturated fatty acids, for example oleic acid, in small amounts, preferably in amounts not above about 2 to 3% by weight. In particular, preference is given to alpha-sulpho fatty acid alkyl esters which have an alkyl chain with not more than 4 carbon atoms in the ester group, for example methyl ester, ethyl ester, propyl ester and butyl ester. With particular advantage, the methyl esters of the alpha-sulpho fatty acids (MES), but also their saponified disalts are used.

Further suitable anionic surfactants are fatty acid derivatives of amino acids, for example of N-methyltaurine (taurides) and/or of N-methylglycine (sarcosides). Particular preference here is given to the sarcosides and/or the sarcosinates and here in particular sarcosinates of higher and optionally mono- or polyunsaturated fatty acids such as oleyl sarcosinate.

Further suitable anionic surfactants are sulphated fatty acid glycerol esters. Fatty acid glycerol esters are to be understood as meaning the mono-, di- and triesters, as well as mixtures thereof, as are obtained during the production by esterification of a monoglycerol with 1 to 3 mol of fatty acid or during the transesterification of triglycerides with 0.3 to 2 mol of glycerol. Preferred sulphated fatty acid glycerol esters here are the sulphation products of saturated fatty acids having 6 to 22 carbon atoms, for example caproic acid, caprylic acid, capric acid, myristic acid, lauric acid, palmitic acid, stearic acid or behenic acid.

Preferred alk(en)yl sulphates are the alkali metal and in particular the sodium salts of the sulphuric acid half-esters of C12-C18-fatty alcohols, for example of coconut fatty alcohol, tallow fatty alcohol, lauryl, myristyl, cetyl or stearyl alcohol or of the C10-C20-oxo alcohols and those half-esters of secondary alcohols of these chain lengths. Furthermore, preference is given to alk(en)yl sulphates of the stated chain length which contain a synthetic, petrochemical-based straight-chain alkyl radical and which have an analogous degradation behaviour to the equivalent compounds based on fatty chemical raw materials. From a washing point of view, the C12-C16-alkyl sulphates and C12-C15-alkyl sulphates, and C14-C15-alkyl sulphates are preferred. 2,3-Alkyl sulphates, which can be obtained for example as commercial products of the Shell Oil Company under the name DAN(R) are also suitable anionic surfactants.

The sulphuric acid monoesters of the straight-chain or branched C7-21-alcohols ethoxylated with 1 to 6 mol of ethylene oxide, such as 2-methyl-branched C9-11-alcohols having on average 3.5 mol of ethylene oxide (EO) or C12-18-fatty alcohols having 1 to 4 EO are also suitable. They are used in cleaners only in relatively small amounts, for example in amounts of from 1 to 5% by weight, on account of their high foaming behaviour.

Further suitable anionic surfactants are also the salts of alkylsulphosuccinic acid, which are also referred to as sulphosuccinates or as sulphosuccinic acid esters and are the monoesters and/or diesters of sulphosuccinic acid with alcohols, preferably fatty alcohols and in particular ethoxylated fatty alcohols. Preferred sulphosuccinates comprise C8-18-fatty alcohol radicals or mixtures of these. Particularly preferred sulphosuccinates contain a fatty alcohol radical which is derived from ethoxylated fatty alcohols which, when viewed per se, are nonionic surfactants (for description see below). Here, particular preference is in turn given to sulphosuccinates whose fatty alcohol radicals are derived from ethoxylated fatty alcohols with a narrowed homologue distribution. It is likewise also possible to use alk(en)ylsuccinic acid having preferably 8 to 18 carbon atoms in the alk(en)yl chain or salts thereof.

Particularly preferred anionic surfactants are soaps. Of suitability are saturated and unsaturated fatty acid soaps, such as the salts of lauric acid, myristic acid, palmitic acid, stearic acid, (hydrogenated) erucic acid and behenic acid, and also in particular soap mixtures derived from natural fatty acids, for example coconut, palm kernel, olive oil or tallow fatty acids.

The anionic surfactants including the soaps can be present in the form of their sodium, potassium or ammonium salts, and also in the form of soluble salts of organic bases, such as mono-, di- or triethanolamine. Preferably, the anionic surfactants are present in the form of their sodium or potassium salts, in particular in the form of the sodium salts.

The content of anionic surfactants in preferred liquid detergents and cleaners is 1 to 30% by weight, preferably 4 to 25% by weight and in particular 5 to 22% by weight, in each case based on the total composition. It is particularly preferred that the amount of fatty acid soap is at least 2% by weight and particularly preferred at least 3% by weight and especially preferred at least 4% by weight.

Suitable further surfactants for producing the detergents or cleaners according to the invention are so-called gemini surfactants. These are generally understood as meaning those compounds which have two hydrophilic groups and two hydrophobic groups per molecule. These groups are generally separated from one another by a so-called "spacer". This spacer is generally a carbon chain which should be long enough for the hydrophilic groups to have a sufficient distance so that they can act independently of one another. Surfactants of this type are characterized in general by an unusually low critical micelle concentration and the ability to greatly reduce the surface tension of the water. In exceptional cases, however, the expression Gemini surfactants is understood as meaning not only dimeric, but also trimeric surfactants.

Gemini surfactants for producing detergents or cleaners are, for example, sulphated hydroxy mixed ethers according to the German patent application DE-A-43 21 022 or dimer alcohol bis- and trimer alcohol tris-sulphates and ether sulphates according to the German patent application DE-A-195 03 061. Terminally capped dimeric and trimeric mixed ethers according to the German patent application DE-A-195 13 391 are characterized in particular by their bi- and multifunctionality. For example, the specified terminally capped surfactants have good wetting properties and in so doing are low-foam, meaning that they are suitable in particular for use in machine washing or cleaning processes.

From an applications point of view, mixtures of anionic and nonionic surfactants are preferred. The total surfactant content of the liquid detergent and cleaner is preferably below 40% by weight and particularly preferably below 35% by weight, based on the total liquid detergent and cleaner.

Builders

Builders which can be present in the liquid detergents and cleaners are, in particular, silicates, aluminium silicates (in particular zeolites), carbonates, organic cobuilders, phosphates, salts of organic di- and polycarboxylic acids, and mixtures of these substances.

Suitable crystalline, layered sodium silicates have the general formula

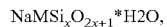

$NaMSi_xO_{2x+1} \cdot H_2O$, where M is sodium or hydrogen, x is a number from 1.9 to 4 and y is a number from 0 to 20 and preferred values for x are 2, 3 or 4. Preferred crystalline sheet silicates of the stated formula are those in which M is sodium and x assumes the values 2 or 3. In particular, preference is given to both beta- and also delta-sodium disilicates $Na_2Si_2O_5 \cdot yH_2O$.

It is also possible to use amorphous sodium silicates with an $Na_2O:SiO_2$ modulus of 1:2 to 1:3.3, preferably from 1:2 to 1:2.8 and in particular from 1:2 to 1:2.6, which have delayed dissolution and secondary detergency properties. The dissolution delay compared with conventional amorphous sodium silicates can have been brought about here in various ways, for example as result of surface treatment, compounding, compaction/compression or as a result of overdrying. In the context of this invention, the term "amorphous" also means "X-ray amorphous". This means that, in X-ray diffraction experiments, the silicates did not produce any sharp X-ray reflections, as are typical for crystalline substances, but at best have one or more maxima of the scattered X-ray radiation, which have a width of several degree units of the diffraction angle. It can, however, very probably even lead to particularly good builder properties if the silicate particles during electron diffraction experiments produce indistinct or even jagged diffraction maxima. This is to be interpreted in such a way that the products have microcrystalline regions of size 10 to a few hundred nm, with values up to at most 50 nm and in particular up to at most 20 nm being preferred. Such so-called X-ray amorphous silicates likewise have a dissolution delay compared with conventional waterglasses. Particular preference is given to compressed/compacted amorphous silicates, compounded amorphous silicates and over dried X-ray amorphous silicates.

A finely crystalline, synthetic zeolite containing bonded water that can be used is preferably zeolite A and/or P. As zeolite P, particular preference is given to zeolite MAP™ (commercial product of Crosfield). However, also of suitability are zeolite X and mixtures of A, X and/or P. Commercially available and usable with preference in the context of the present invention is for example also a cocrystallizate of zeolite X and zeolite A (about 80% by weight zeolite X), which is sold by SASOL under the trade name VEGOBOND AX(R) and can be described by the formula $$n\text{Na}_2\text{O}*(1-n)\text{K}_2\text{O}*\text{Al}_2\text{O}_3.(2\text{-}2.5)*\text{SiO}_2.(3.5\text{-}5.5)*\text{H}_2\text{O}.$$

The zeolite can be used in the form of a spray-dried powder or else as an undried, stabilized suspension that is still wet from its preparation. If the zeolite is used as a suspension, this can comprise small additives of nonionic surfactants as stabilizers, for example 1 to 3% by weight, based on zeolite, of ethoxylated $C_{12}$-$C_{18}$-fatty alcohols with 2 to 5 ethylene oxide groups, $C_{12}$-$C_{14}$-fatty alcohols with 4 to 5 ethylene oxide groups or ethoxylated isotridecanols. Suitable zeolites have an average particle size of less than 10 μm (volume distribution; measurement method: Coulter counter) and comprise preferably 18 to 22% by weight, in particular 20 to 22% by weight, of bonded water.

It is of course also possible to use the generally known phosphates as builder substances provided such a use should not be avoided for ecological reasons. Of suitability are in particular the sodium salts of the orthophosphates, the pyrophosphates and in particular the tripolyphosphates.

Suitable builders are organic cobuilders, in particular polycarboxylates/polycarboxylic acids, polymeric polycarboxylates, aspartic acid, polyacetals, dextrins, and phosphonates.

Polymeric polycarboxylates are for example the alkali metal salts of polyacrylic acid or of polymethacrylic acid, for example those with a relative molecular mass of from 500 to 70 000 g/mol. The molar masses stated for polymeric polycarboxylates in the context of this specification are weight-average molar masses Mw of the particular acid form, which have been determined in principle by means of gel permeation chromatography (GPC), using a UV detector. The measurement was carried out here against an external polyacrylic acid standard, which produces realistic molecular weight values on account of its structural similarity to the investigated polymers. This data differs significantly from molecular weight data for which polystyrene sulphonic acids are used as the standard. The molar masses measured against polystyrene sulphonic acids are generally considerably higher than the molar masses stated in this specification.

Suitable polymers are in particular polyacrylates, which preferably have a molecular mass of from 2000 to 20 000 g/mol. On account of their superior solubility the short-chain polyacrylates, which have molar masses of from 2000 to 10 000 g/mol, and particularly preferably from 3000 to 5000 g/mol, can in turn be preferred from this group.

Also of suitability are copolymeric polycarboxylates, in particular those of acrylic acid with methacrylic acid and of acrylic acid or methacrylic acid with maleic acid. Copolymers of acrylic acid with maleic acid which comprise 50 to 90% by weight of acrylic acid and 50 to 10% by weight of maleic acid have proven to be particularly suitable. Their relative molecular mass, based on free acids, is generally 2000 to 70 000 g/mol, preferably 20 000 to 50 000 g/mol and in particular 30 000 to 40 000 g/mol.

Of particular preference are also biodegradable polymers of more than two different monomer units, for example those which comprise, as monomers, salts of acrylic acid and of maleic acid, and also vinyl alcohol or vinyl alcohol derivatives or which comprise, as monomers, salts of acrylic acid and of 2-alkylallylsulphonic acid, and sugar derivatives.

Further preferred copolymers are those which have, as monomers, preferably acrolein and acrylic acid/acrylic acid salts or acrolein and vinyl acetate.

Polymeric aminodicarboxylic acids, salts thereof or precursor substances thereof are likewise to be mentioned as further preferred builder substances. Of particular preference are polyaspartic acids and salts and derivatives thereof which, besides cobuilder properties, also have a bleach-stabilizing effect.

Further suitable builder substances are polyacetals which can be obtained by reacting dialdehydes with polyolcarboxylic acids which have 5 to 7 carbon atoms and at least 3 hydroxyl groups. Preferred polyacetals are obtained from dialdehydes such as glyoxal, glutaraldehyde, terephthalaldehyde, and mixtures thereof and from polyolcarboxylic acids such as gluconic acid and/or glucoheptonic acid.

Further suitable organic builder substances are dextrins, for example oligomers and polymers of carbohydrates which can be obtained by partial hydrolysis of starches. The hydrolysis can be carried out according to customary, for example acid- or enzyme-catalysed, processes. The hydrolysis products are preferably those with average molar masses in the range from 400 to 500 000 g/mol. Here, a polysaccharide with a dextrose equivalent (DE) in the range from 0.5 to 40, in particular from 2 to 30, is preferred, with DE being a customary measure of the reducing effect of a polysaccharide compared to dextrose, which has a DE of 100. It is possible to use either maltodextrins with a DE between 3 and 20 and dry glucose syrups with a DE between 20 and 37 or so-called yellow dextrins and white dextrins with higher molar masses in the range from 2000 to 30 000 g/mol.

The oxidized derivatives of such dextrins are the reaction products thereof with oxidizing agents, which are able to oxidize at least one alcohol function of the saccharide ring to the carboxylic acid function. A product oxidized on C6 of the saccharide ring can be particularly advantageous.

A preferred dextrin is described in the British patent application GB 9,419,091 B1. The oxidized derivatives of such dextrins are their reaction products with oxidizing agents which are able to oxidize at least one alcohol function of the saccharide ring to the carboxylic acid function. Oxidized dextrins of this type and processes for their preparation are known for example from the European patent applications EP 032202 A, EP 0427349 A, EP 0472042 A and EP 0542496 A, and the international patent applications WO 1992/018542 A, WO 1993/008251 A, WO 1994/028030 A, WO 1995/007303 A, WO 1995/012619 A and WO 1995/020608 A. A product oxidized on $C_6$ of the saccharide ring can be particularly advantageous.

Oxydisuccinates and other derivatives of disuccinates, preferably ethylenediamine disuccinate, are also further suitable cobuilders. Here, ethylenediamine N,N'-disuccinate (EDDS) is preferably used in the form of its sodium or magnesium salts. Furthermore, preference is given in this connection also to glycerol disuccinates and glycerol trisuccinates, as are described for example in the US-American patent specifications U.S. Pat. Nos. 4,524,009, 4,639,325, in the European patent application EP 0150930 A and the Japanese patent application JP 1993/339896 A.

Further organic cobuilders that can be used are, for example, acetylated hydroxycarboxylic acids and salts thereof, which can optionally also be present in lactone form and which contain at least 4 carbon atoms and at least one hydroxy group, and at most two acid groups. Cobuilders of this kind are described for example in the International patent application WO 1995/020029 A.

A further substance class with cobuilder properties is the phosphonates. These are in particular hydroxyalkane- and aminoalkanephosphonates. Among the hydroxyalkanephosphonates, 1-hydroxyethane-1,1-diphosphonate (HEDP) is of particular importance as cobuilder. It is preferably used as sodium salt, with the disodium salt giving a neutral reaction and the tetrasodium salt giving an alkaline (pH 9) reaction. Suitable aminoalkanephosphonates are preferably ethylenediaminetetramethylenephosphonate (EDTMP), diethylenetriaminepentamethylenephosphonate (DTPMP), and higher homologues thereof. They are preferably used in the form of the neutral reacting sodium salts, e.g. as hexasodium salt of EDTMP or as hepta- and octa-sodium salt of DTPMP. The builder used here from the class of phosphonates is preferably HEDP. The aminoalkanephosphonates, moreover, have a marked heavy metal binding capacity. Accordingly, it may be preferred, especially if the detergents and cleaners also comprise bleach, to use aminoalkanephosphonates, in particular DTPMP, or to use mixtures of the stated phosphonates for producing the composition.

Moreover, all compounds which are able to form complexes with alkaline earth metal ions can be used as cobuilders.

Further organic builder substances that can be used are also the polycarboxylic acids that can be used in the form of their sodium salts, with polycarboxylic acids being understood as meaning those carboxylic acids which carry more than one acid function. For example, these are citric acid, adipic acid, succinic acid, glutaric acid, malic acid, tartaric acid, maleic acid, fumaric acid, sugar acids, aminocarboxylic acids, nitrilotriacetic acid (NTA), provided such a use is not objectionable for ecological reasons, and mixtures of these. Preferred salts are the salts of the polycarboxylic acids such as citric acid, adipic acid, succinic acid, glutaric acid, tartaric acid, sugar acids and mixtures of these.

The acids per se can also be used. Besides their builder effect, the acids typically also have the property of an acidifying component and thus also serve to establish a lower and more mild pH of detergents and/or cleaners. In particular, mention is to be made here of citric acid, succinic acid, glutaric acid, adipic acid, gluconic acid and any desired mixtures of these.

Bleaches and Bleach Catalysts

Among the compounds which produce H2O2 in water and serve as bleaches, sodium perborate tetrahydrate and sodium perborate monohydrate have particular importance. Further bleaches that can be used are, for example, sodium percarbonate, peroxypyrophosphates, citrate perhydrates, and also H2O2-producing peracidic salts or peracids, such as perbenzoates, peroxophthalates, diperazelaic acid, phthaloiminoperacid or diperdodecanedioic acid. In order to achieve an improved bleaching effect upon washing at temperatures of 60° C. and below, bleach activators can be incorporated into the detergents and cleaners. Bleach activators that can be used are compounds which, under perhydrolysis conditions, produce aliphatic peroxocarboxylic acids having preferably 1 to 10 carbon atoms, in particular 2 to 4 carbon atoms, and/or optionally substituted perbenzoic acid. Of suitability are substances which carry the O- and/or N-acyl groups of the stated number of carbon atoms and/or optionally substituted benzoyl groups. Preference is given to polyacylated alkylene diamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenol sulphonates, in particular nonanoyl- or isononanoyloxybenzene sulphonate (n- or iso-NOBS), carboxylic acid anhydrides, in particular phthalic anhydride, acylated polyhydric alcohols, in particular triacetin, ethylene glycol diacetate and 2,5-diacetoxy-2,5-dihydrofuran. In addition to the conventional bleach activators or instead of them, it is also possible for so-called bleach catalysts to be incorporated into the textile treatment compositions. These substances are bleach-enhancing transition metal salts or transition metal complexes such as, for example, Mn-, Fe-, Co-, Ru- or Mo-salen complexes or -carbonyl complexes. Mn, Fe, Co, Ru, Mo, Ti, V and Cu complexes with nitrogen-containing tripod ligands, and Co-, Fe-, Cu- and Ru-ammine complexes can also be used as bleach catalysts.

Thickeners

A liquid detergent and cleaner can comprise a thickener. The thickener can comprise, for example, a polyacrylate thickener, xanthan gum, gellan gum, guar seed flour, alginate, carrageenan, carboxymethylcellulose, bentonite, wellan gum, carob seed flour, agar agar, tragacanth, gum arabic, pectins, polyoses, starch, dextrins, gelatine and casein. However, modified natural substances such as modified starches and celluloses can also be used as thickeners, examples here being carboxymethylcellulose and other cellulose ethers, hydroxyethyl- and -propylcellulose, and seed flour ethers.

The polyacrylic and polymethacrylic thickeners include, for example, the high molecular weight homopolymers of acrylic acid crosslinked with a polyalkenyl polyether, in particular an allyl ether of sucrose, pentaerythritol or propylene (INCI name according to "International Dictionary of Cosmetic Ingredients" of The Cosmetic, Toiletry and Fragrance Association (CTFA): Carbomer), which are also referred to as carboxyvinyl polymers. Such polyacrylic acids are available inter alia from 3V Sigma under the trade name Polygel®, e.g. Polygel DA, and from B.F. Goodrich under the trade name Carbopol®, e.g. Carbopol 940 (molecular weight about 4 000 000), Carbopol 941 (molecular weight about 1 250 000) or Carbopol 934 (molecular weight about 3 000 000). Furthermore, these include the following acrylic acid copolymers: (i) copolymers of two or more monomers from the group of acrylic acid, methacrylic acid and its simple esters formed preferably with C1-4-alkanols (INCI Acrylates Copolymer), which include for example the copolymers of methacrylic acid, butyl acrylate and methyl methacrylate (CAS name according to Chemical Abstracts Service: 25035-69-2) or of butyl acrylate and methyl methacrylate (CAS 25852-37-3) and which are available for example by Rohm and Haas under the trade names Aculyn® and Acusol®, and also by Degussa (Goldschmidt) under the trade name Tego® Polymer, e.g. the anionic nonassociative polymers Aculyn 22, Aculyn 28, Aculyn 33 (crosslinked), Acusol 810, Acusol 820, Acusol 823 and Acusol 830 (CAS 25852-37-3); (ii) crosslinked high molecular weight acrylic acid copolymers, which include for example the copolymers, crosslinked with an allyl ether of sucrose or of pentaerythritol, of C10-30-alkyl acrylates with one or more monomers from the group of acrylic acid, methacrylic acid and their simple esters, formed preferably with C1-4-alkanols (INCI Acrylates/C10-30 Alkyl Acrylate Crosspolymer) and which are available for example from B.F. Goodrich under the trade name Carbopol®, e.g. the hydrophobicized Carbopol ETD 2623 and Carbopol 1382 (INCI Acrylates/C10-30 Alkyl Acrylate Crosspolymer), and Carbopol Aqua 30 (formerly Carbopol EX 473).

A further polymeric thickener to be used with preference is xanthan gum, a microbial anionic heteropolysaccharide which is produced from *xanthomonas campestris* and a few other species under aerobic conditions and has a molar mass of from 2 to 15 million Daltons. Xanthan is formed from a chain with beta-1,4-bonded glucose (cellulose) with side chains. The structure of the subgroups consists of glucose, mannose, glucuronic acid, acetate and pyruvate, where the number of pyruvate units determines the viscosity of the xanthan gum. Suitable thickeners are in particular also a fatty alcohol. Fatty alcohols can be branched or unbranched and of native origin or petrochemical origin. Preferred fatty alcohols have a carbon chain length of from 10 to 20 carbon atoms, preferably 12 to 18. Preference is given to using mixtures of different carbon chain lengths, such as tallow fatty alcohol or coconut fatty alcohol. Examples are Lorol® Spezial (C12-14-ROH) or Lorol® Technisch (C12-18-ROH) (both from Cognis). Preferred liquid detergents and cleaners comprise, based on the total composition, 0.01 to 3% by weight and preferably 0.1 to 1% by weight, of thickeners. The amount of thickener used here is dependent on the type of thickener and the desired degree of thickening.

Enzymes

The detergents and cleaners can comprise enzymes in encapsulated form and/or directly in the detergents and cleaners. Suitable enzymes are in particular those from the classes of the hydrolases, such as the proteases, esterases, lipases or lipolytically active enzymes, amylases, cellulases or other glycosyl hydrolases, hemicellulase, cutinases, beta-glucanases, oxidases, peroxidases, perhydrolases and/or laccases and mixtures of said enzymes. All of these hydrolases contribute in the washing to the removal of stains such as protein-, grease- or starch-containing stains and grey discolorations. Cellulases and other glycosyl hydrolases can, moreover, contribute as result of the removal of pilling and microfibrills to colour retention and to increasing the softness of the textile. Oxidoreductases can also be used for bleaching and/or for inhibiting colour transfer. Of particularly good suitability are enzymatic active ingredients obtained from bacteria strains or fungi such as *Bacillus subtilis, Bacillus licheniformis, Streptomyceus griseus* and *Humicola insolens*. Preference is given to using proteases of the subtilisin type and in particular proteases which are obtained from *Bacillus lentus*. Here, enzyme mixtures, for example of protease and amylase or protease and lipase or lipolytically active enzymes or protease and cellulase or from cellulase and lipase or lipolytically active enzymes or from protease, amylase and lipase or lipolytically active enzymes or protease, lipase or lipolytically active enzymes and cellulase, but in particular protease and/or lipase-containing mixtures or mixtures with lipolytically active enzymes are of particular interest. Examples of such lipolytically active enzymes are the known cutinases. Peroxidases or oxidases have also in some cases proven to be suitable. Suitable amylases include in particular alpha-amylases, isoamylases, pullulanases and pectinases. The cellulases used are preferably cellobiohydrolases, endoglucanases and p-glucosidases, which are also called cellobiases, or mixtures of these. Since different cellulase types differ by virtue of their CMCase and avicelase activities, the desired activities can be established through targeted mixtures of the cellulases.

The enzymes can be adsorbed to carrier substances in order to protect them from premature decomposition. The fraction of the enzymes, of the enzyme liquid formulation(s) or of the enzyme granules directly in detergents and cleaners can be for example about 0.01 to 5% by weight, preferably 0.12 to about 2.5% by weight.

However, it may also be preferred, for example in the case of special detergents and cleaners for consumers with allergies, that the detergent and cleaner comprises no enzymes.

Electrolytes

A broad number of highly diverse salts can be used as electrolytes from the group of the inorganic salts. Preferred cations are the alkali metal and alkaline earth metals, preferred anions are the halides and sulphates. From a production point of view, the use of NaCl or $MgCl_2$ in the detergents and cleaners is preferred. The fraction of electrolytes in the detergents and cleaners is usually 0.1 to 5% by weight.

Solvents

Nonaqueous solvents which can be used in the liquid detergents and cleaners originate for example from the group of the mono- or polyhydric alcohols, alkanolamines or glycol ethers, provided they are miscible with water in the stated concentration range. The solvents are preferably selected from ethanol, n- or isopropanol, butanols, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or -ethyl ether, diisopropylene glycol monomethyl or -ethyl ether, methoxy-, ethoxy- or butoxytriglycol, 1-butoxyethoxy-2-propanol, 3-methyl-3-methoxybutanol, propylene glycol t-butyl ether, and mixtures of these solvents. Nonaqueous solvents can be used in the liquid detergents and cleaners in amounts between 0.5 and 15% by weight, but preferably below 12% by weight and in particular below 9% by weight.

Viscosity

The viscosity of the detergents and cleaners in liquid form can be measured using customary standard methods (for example Brookfield viscometer LVT-II at 20 rpm and 20° C., spindle 3) and is for liquid detergents preferably in the range from 500 to 5000 mPas. Preferably, liquid detergents and cleaners have viscosities of from 700 to 4000 mPas, with values between 1000 and 3000 mPas being particularly preferred. The viscosity of fabric softeners is preferably 20 to 4000 mPas, with values between 40 and 2000 mPas being particularly preferred. The viscosity of fabric softeners is particularly preferably from 40 to 1000 mPas.

pH Regulators

In order to bring the pH of the liquid detergents and cleaners into the desired range, the use of pH regulators may be appropriate. Here, it is possible to use all known acids or alkalis provided their use is not ruled out for application-related or ecological reasons or for reasons of consumer protection. Usually, the amount of these extenders does not exceed 7% by weight of the total formulation. The pH of liquid detergents and cleaners is preferably between 4 and 10 and preferably between 5.5 and 8.5. The pH of liquid fabric softeners is preferably between 1 and 6 and preferably between 1.5 and 3.5.

Dyes

In order to improve the aesthetic impression of the textile treatment compositions, they can be coloured with suitable dyes. Preferred dyes, the selection of which does not present the person skilled in the art with any difficulty, have a high storage stability and insensitivity to the other ingredients of the detergents and cleaners and to light and no marked substantivity towards textile fibres, so as not to stain these.

Antiredeposition Agents

Suitable soil release polymers, which are also referred to as "antiredeposition agents", are for example nonionic cellulose ethers such as methyl cellulose and methylhydroxypropyl cellulose with a fraction of methoxy groups of from 15 to 30% by weight and of hydroxypropyl groups of from 1 to 15% by weight, in each case based on the nonionic cellulose ethers, as well as the polymers, known from the prior art, of phthalic acid and/or terephthalic acid or of derivatives thereof, in particular polymers of ethylene terephthalates and/or polyethylene and/or polypropylene glycol terephthalates or anionically and/or nonionically modified derivatives of these. Suitable derivatives include the sulphonated derivatives of phthalic acid and terephthalic acid polymers.

Optical Brighteners

Optical brighteners (so-called "white toners") can be added to the detergents and cleaners in order to eliminate greying and yellowing of the treated fabrics. These substances attach to the fibres and bring about a lightening and pretend bleaching effect by converting invisible ultraviolet radiation into visible long-wave light, the ultraviolet light absorbed from the sunlight being irradiated as slightly bluish fluorescence and producing pure white with the yellow shade of the greyed or yellowed laundry. Suitable compounds originate for example from the substance classes of the 4,4'-diamino-2,2'-stilbenedisulphonic acids (flavone acids), 4,4'-distyrylbiphenyls, methylumbelliferones, coumarins, dihydroquinolinones, 1,3-diarylpyrazolines, naphthalimides, benzoxazole, benzisoxazole and benzimidazole systems, as well as the pyrene derivatives substituted by heterocycles. The optical brighteners are usually used in amounts between 0% and 0.3% by weight, based on the finished detergent and cleaner.

Greying Inhibitors

Greying inhibitors have the task of keeping the dirt detached from the fibres suspended in the liquor and in so doing of preventing reattachment of the dirt. For this purpose, water-soluble colloids of a mostly organic nature are suitable, for example size, gelatine, salts of ether sulphonic acids or starch or of cellulose or salts of acidic sulphuric acid esters of cellulose or of starch. Water-soluble polyamides containing acidic groups are also suitable for this purpose. Furthermore, it is possible to use soluble starch preparations and starch products other than those specified above, for example degraded starch, aldehyde starches etc. Polyvinylpyrrolidone can also be used. However, preference is given to using cellulose ethers such as carboxymethylcellulose (Na salt), methylcellulose, hydroxyalkylcellulose and mixed ethers such as methylhydroxyethylcellulose, methylhydroxypropylcellulose, methylcarboxymethylcellulose and mixtures thereof in amounts of from 0.1 to 5% by weight, based on the detergents and cleaners.

Anticrease Agents

Since fabrics, in particular made of rayon, spun rayon, cotton and mixtures thereof, can have a tendency to crease because the individual fibres are sensitive to bending, crinkling, pressing and squashing transverse to the fibre direction, the detergents and cleaners can comprise synthetic anticrease agents. These include, for example, synthetic products based on fatty acids, fatty acid esters, fatty acid amides, fatty acid alkylol esters, fatty acid alkylolamides or fatty alcohols, which are mostly reacted with ethylene oxide, or products based on lecithin or modified phosphoric acid esters.

Antimicrobial Active Ingredients

To control microorganisms, the detergents and cleaners can comprise antimicrobial active ingredients. A distinction is made here, according to the antimicrobial spectrum and mechanism of action, between bacteriostats and bactericides, fungistats and fungicides etc. Important substances from these groups are, for example, benzalkoniumchlorides, alkylarylsulphonates, halophenols and phenolmercuriacetate, it also being possible to dispense entirely with these compounds in the case of the detergents and cleaners according to the invention.

Preservatives

The detergents and cleaners according to the invention can comprise preservatives, in which case preferably only those are used which have, if any, only a slight skin-sensitizing potential. Examples are sorbic acid and its salts, benzoic acid and its salts, salicylic acid and its salts, phenoxyethanol, 3-iodo-2-propynyl butylcarbamate, sodium N-(hydroxymethyl)glycinate, biphenyl-2-ol, and mixtures thereof. A suitable preservative is the solvent-free, aqueous combination of diazolidinylurea, sodium benzoate and potassium sorbate (available as Euxyl® K 500ex Schülke and Mayr), which can be used in a pH range up to 7. Of particular suitability are preservatives based on organic acids and/or salts thereof for preserving the skin-friendly detergents and cleaners according to the invention.

Antioxidants

In order to prevent undesired changes to the detergents and cleaners and/or the treated fabrics caused by the action of oxygen and other oxidative processes, the detergents and cleaners can comprise antioxidants. This compound class includes, for example, substituted phenols, hydroquinones, pyrocatechins and aromatic amines, and also organic sulphides, polysulphides, dithiocarbamates, phosphites, phosphonates and vitamin E.

Antistatic Agents

Increased wear comfort can result from the additional use of antistatic agents which are additionally added to the detergents and cleaners. Antistatic agents increase the surface conductivity and thus allow an improved discharging of charges formed. Antistatic agents are generally substances with at least one hydrophilic molecular ligand and give a more or less hygroscopic film on the surfaces. These mostly interface-active antistatic agents can be divided into nitrogen-containing ones (amines, amides, quaternary ammonium compounds), phosphorus-containing ones (phosphoric acid esters) and sulphur-containing ones (alkylsulphonates, alkylsulphates). Lauryl-(or stearyl-)dimethylbenzylammonium chlorides are suitable as antistatic agents for fabrics and/or as additive for detergents and cleaners, in which case a finishing effect is additionally achieved.

Foam Inhibitors

To improve the rewettability of the treated fabrics and to facilitate ironing of the treated fabrics, silicone derivatives, for example, can be used in the textile treatment compositions. These additionally improve the rinse-out behaviour of the detergents and cleaners by virtue of their foam-inhibiting properties. Preferred silicone derivatives are, for example, polydialkyl- or alkylarylsiloxanes in which the alkyl groups have one to five carbon atoms and are completely or partially fluorinated. Preferred silicones are polydimethylsiloxanes, which can optionally be derivatized and are then amino functional or quaternized and/or have Si—OH, Si—H and/or Si—Cl bonds. The viscosities of the preferred silicones at 25° C. are in the range between 100 and 100 000 mPas, where the silicones can be used in amounts between 0.2 and 5% by weight, based on the total detergent and cleaner.

UV Absorbers

Finally, the detergents and cleaners can also comprise UV absorbers, which attach to the treated fabrics and improve the light resistance of the fibres. Compounds which have these desired properties are, for example, the compounds effective as a result of radiationless deactivation and derivatives of benzophenone with substituents in the 2 and/or 4 position. Furthermore of suitability are also substituted benzotriazoles, 3-phenyl-substituted acrylates (cinnamic acid derivatives), optionally with cyano groups in the 2 position, salicylates, organic Ni complexes, and natural substances such as umbelliferone and endogeneous urocanic acid.

Heavy Metal Complexing Agents

In order to avoid the decomposition of certain detergent ingredients catalysed by heavy metals, it is possible to use substances which complex heavy metals. Suitable heavy metal complexing agents are, for example, the alkali metal salts of ethylenediaminetetraacetic acid (EDTA) or of nitrilotriacetic acid (NTA), and also alkali metal salts of anionic polyelectrolytes such as polymaleates and polysulphonates. A preferred class of complexing agents is the phosphonates, which are present in preferred textile treatment compositions in amounts of from 0.01 to 2.5% by weight, preferably 0.02 to 2% by weight and in particular from 0.03 to 1.5% by weight. These preferred compounds include in particular organo-phosphonates such as, for example, 1-hydroxyethane-1,1-diphosphonic acid (HEDP), aminotri(methylenephosphonic acid) (ATMP), diethylenetriaminepenta(methylenephosphonic acid) (DTPMP or DETPMP), and 2-phosphonobutane-1,2,4-tricarboxylic acid (PBS-AM), which are mostly used in the form of their ammonium or alkali metal salts.

Producing the Preparations

The liquid laundry detergents, dishwashing detergents and cleaners are produced using customary and known methods and processes in which, for example, the constituents are simply mixed in stirred tanks, with water, nonaqueous solvents and surfactants expediently being added as initial charge and the other constituents being added in portions. Thus, liquid detergents and cleaners can be produced by initially introducing the acidic components such as, for example, the linear alkylsulphonates, citric acid, boric acid, phosphonic acid, the fatty alcohol ether sulphates, etc. and the nonionic surfactants. The solvent component is preferably also added at this point, although the addition can also take place at a later time. The polyacrylate is added to these components. Then, a base such as, for example, NaOH, KOH, triethanolamine or monoethanolamine is added, followed by the fatty acid, if present. Subsequently, the remaining ingredients and the remaining solvents of the aqueous liquid detergents and cleaners are added to the mixture and the pH is adjusted to approximately 8.5. Finally, the particles to be dispersed can be added and distributed homogeneously in the aqueous liquid detergent and cleaner by mixing.

The compositions according to the invention are preferably laundry detergents which are suitable both for manual for machine washing, in particular of textiles. They may also be detergents or cleaners for the industrial sector or for the household sector. Cleaners can be used for example also for cleaning hard surfaces. These may for example be dishwashing detergents which are used for the manual or machine cleaning of dishes. They may also be customary industrial or household cleaners with which hard surfaces such as furniture surfaces, tiles, wall and floor coverings are cleaned. Besides dishes, hard surfaces also include all customary hard surfaces, in particular made of glass, ceramic, plastic or metal, domestically and in industry.

Here, the detergents and cleaners are preferably liquid formulations which may be solutions, emulsions, dispersions, suspensions, microemulsions, gels or pastes.

As surface treatment agents, the composition can accordingly comprise customary ingredients of cleaners in customary amounts. For example, surface treatment compositions in the form of cleaners can comprise alkyl ether sulphates, alkyl- and/or arylsulphonates, alkyl sulphates, amphoteric surfactants, anionic surfactants, nonionic surfactants, cationic surfactants, solvents, thickeners, dicarboxylic acid (salts) and further auxiliaries and additives.

These additional ingredients have in part already been explained in more detail above and are likewise valid here for use in cleaners (see e.g. nonionic surfactants). Auxiliaries and additives which may be present—especially in hand dishwashing detergents and cleaners for hard surfaces—are in particular UV stabilizers, perfume, pearlizing agents (INCI Opacifying Agents; for example glycol distearate, e.g. Cutina® AGS from Henkel KGaA, or mixtures containing this, e.g. the Euperlans® from Henkel KGaA), SRP (soil repellent polymers), PEG terephthalates, dyes, bleaches (e.g. hydrogen peroxide), corrosion inhibitors, preservatives (e.g. the 2-bromo-2-nitropropane-1,3-diol technically also referred to as bronopol (CAS 52-51-7), which is commercially available for example as Myacide® BT or as Boots-Bronopol BT from Boots), and skin-feel-improving or care additives (e.g. dermatologically effective substances such as vitamin A, vitamin B2, vitamin B12, vitamin C, vitamin E, D-panthenol, sericerin, collagen partial hydrolysate, various plant protein partial hydrolysates, protein hydrolysate fatty acid condensates, liposomes, polypropylene glycol, Nutrilan™ Chitosan™, cholesterol, vegetable and animal oils such as e.g. lecithin, soybean oil, etc., plant extracts such as e.g. aloe vera, azulene, hamamelis extracts, algae extracts, etc., allantoin, A.H.A. complexes, in amounts of usually not more than 5% by weight. To enhance performance, small amounts of enzymes can be used. Preference is given to proteases (e.g. BLAP (Henkel), savinase (NOVO), durazym (NOVO), maxapemm, etc.), amylases (e.g. fermamyl (NOVO), etc.), lipases (e.g. lipolase (NOVO), etc.), peroxidases, gluconases, cellulases, mannases, etc., in amounts of preferably 0.001 to 1.5% by weight and particularly preferably less than 0.5% by weight.

Cosmetic Preparations

A further subject matter of the invention relates to cosmetic preparations at least four lactones selected from the group consisting of γ-hexalactone, γ-heptalactone, γ-octalactone, γ-nonalactone, γ-decalactone, γ-undecalactone, γ-dodecalactone, δ-hexalactone, δ-heptalactone, δ-octalactone, δ-nonalactone, δ-decalactone, δ-undecalactone, δ-dodecalactone, and mixtures thereof, where the use concentration of the lactone or of the lactones is usually in the range from 0.01 to 1% by weight, preferably 0.1 to 0.5% by weight—based on the preparations.

The cosmetic compositions according to the invention can comprise further typical auxiliaries and additives, such as, for example, mild surfactants, oil bodies, emulsifiers, pearlescent waxes, consistency regulators, thickeners, superfatting agents, stabilizers, polymers, silicone compounds, fats, waxes, lecithins, phospholipids, UV light protection factors, humectants, biogenic active ingredients, antioxidants, deodorants, antiperspirants, antidandruff agents, film formers, swelling agents, insect repellants, self-tanning agents, tyrosine inhibitors (depigmentation agents), hydrotropes, solubilizers, preservatives, perfume oils, dyes and the like.

Surfactants

Surface-active substances that can be present are anionic, nonionic, cationic and/or amphoteric or zwitterionic surfactants, the fraction of which in the compositions is usually about 1 to 70, preferably 5 to 50 and in particular 10 to 30% by weight. Typical examples of anionic surfactants are soaps, alkylbenzenesulphonates, alkanesulphonates, olefinsulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulphates, protein fatty acid condensates (in particular plant products based on wheat) and alkyl(ether) phosphates. If the anionic surfactants contain polyglycol ether chains, these can have a conventional homologue distribution, but preferably have a narrowed homologue distribution. Typical examples of nonionc surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolysates (in particular plant products based on wheat), polyol fatty acid esters, sugar esters, sorbitan esters, polysorbates and amine oxides. If the nonionic surfactants contain polyglycol ether chains, these can have a conventional homologue distribution, but preferably have a narrowed homologue distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulphobetaines. Said surfactants are exclusively known compounds. Typical examples of particularly suitable mild, i.e. particularly skin-compatible surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, α-olefin sulphonates, ethercarboxylic acids, alkyl oligoglucosides, fatty acid glucamides, alkylamidobetaines, amphoacetals and/or protein fatty acid condensates, the latter preferably based on wheat proteins.

Oil Bodies

Suitable oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also of suitability are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as e.g. propylene glycol, dimer diol or trimer triol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as e.g. dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as e.g. dicaprylyl ether (Cetiol® OE), ring-opening products of epoxidized fatty acid esters with polyols, silicone oils (cyclomethicones, silicon methicone types etc.) and/or aliphatic or naphthenic hydrocarbons, such as e.g. squalane, squalene or dialkylcyclohexanes.

Emulsifiers

Suitable emulsifiers are, for example, nonionogenic surfactants from at least one of the following groups:
  addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkyl phenols having 8 to 15 carbon atoms in the alkyl group, and alkylamines having 8 to 22 carbon atoms in the alkyl radical;
  alkyl and/or alkenyl oligoglycosides having 8 to 22 carbon atoms in the alk(en)yl radical and ethoxylated analogues thereof;
  addition products of from 1 to 15 mol of ethylene oxide onto castor oil and/or hydrogenated castor oil;
  addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and adducts thereof having 1 to 30 mol of ethylene oxide;

partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof having 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol.

mono-, di- and trialkyl phosphates, and mono-, di- and/or tri-PEG alkyl phosphates and salt thereof;

wool wax alcohols;

polysiloxane-polyalkyl-polyether copolymers and corresponding derivatives;

block copolymers e.g. polyethylene glycol-30 dipolyhydroxystearates;

polymer emulsifiers, e.g. Pemulen grades (TR-1, TR-2) from Goodrich or Cosmedia® SP from Cognis;

polyalkylene glycols, and glycerol carbonate.

Particularly suitable emulsifiers are explained in more detail below:

Alkoxylates.

The addition products of ethylene oxide and/or of propylene oxide onto fatty alcohols, fatty acids, alkyl phenols or onto castor oil are known, commercially available products. These are homologue mixtures, the average degree of alkoxylation of which corresponds to the ratio of the quantitative amounts of ethylene oxide and/or propylene oxide and substrate with which the addition reaction is carried out. $C_{12/18}$-Fatty acid mono- and diesters of addition products of ethylene oxide onto glycerol are known as re-fatting agents for cosmetic preparations.

Alkyl and/or alkenyl oligoglycoside. Alkyl and/or alkenyl oligoglycosides, their preparation and their use are known from the prior art. Their preparation takes place in particular by reacting glucose or oligosaccharides with primary alcohols having 8 to 18 carbon atoms. As regards the glycoside radical, both monoglycosides in which a cyclic sugar radical is bonded glycosidically to the fatty alcohol, as well as oligomeric glycosides with a degree of oligomerization to preferably about 8 are suitable. The degree of oligomerization here is a statistical average value which has as its basis a homologue distribution customary for such technical products.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and technical-grade mixtures thereof which can also contain small amounts of triglyceride in secondary amounts from the preparation process. Likewise of suitability are addition products of from 1 to 30, preferably 5 to 10, mol of ethylene oxide onto the stated partial glycerides.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise of suitability are addition products of from 1 to 30, preferably 5 to 10, mol of ethylene oxide onto the stated sorbitan esters.

Polyglycerol esters. Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methyl glucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic emulsifiers. Typical anionic emulsifiers are aliphatic fatty acids having 12 to 22 carbon atoms, such as, for example, palmitic acid, stearic acid or behenic acid, and also dicarboxylic acids having 12 to 22 carbon atoms, such as, for example, azelaic acid or sebacic acid.

Amphoteric and cationic emulsifiers. Furthermore, zwitterionic surfactants can be used as emulsifiers. Zwitterionic surfactants is the term used to refer to those surface-active compounds which carry at least one quaternary ammonium group and at least one carboxylate and one sulphonate group in the molecule. Particularly suitable zwitterionic surfactants are the so-called betaines such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxylmethyl-3-hydroxyethylimidazolines having in each case 8 to 18 carbon atoms in the alkyl or acyl group, as well as cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. Ampholytic surfactants are understood as meaning those surface-active compounds which, apart from a $C_{8/18}$-alkyl or acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, suitable emulsifiers are also cationic surfactants, with those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, and suitable waxes are inter alia natural waxes, such as e.g. candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial grease, ceresine, ozokerite (earth wax), petrolatum, paraffin waxes, microwaxes; chemically modified waxes (hard waxes), such as e.g. montan ester waxes, sasol waxes, hydrogenated jojoba waxes, and synthetic waxes, such as e.g. polyalkylene waxes and polyethylene glycol waxes. Besides the fats, suitable additional substances are also fat-like substances, such as lecithins and phospholipids. The term lecithins is understood by the person skilled in the art as meaning those glycero-phospholipids which are formed from fatty acids, glycerol, phosphoric acid and cholin by esterification. Lecithins are therefore also often referred to as phosphatidylcholines (PC) in the specialist world. Examples of natural lecithins that may be mentioned are the kephalins, which are also referred to as phosphatidic acids and are derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed among the fats. In addition, sphingosines and sphingolipids are also suitable.

Pearlescent Waxes

Suitable pearlescent waxes are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Cooling Substances

Cooling substances are compounds which produce a feeling of coldness on the skin. As a rule, these are menthol compounds which—besides the basic body menthol itself—are selected for example from the group which is formed by Menthol Methyl Ether, Menthone Glyceryl Acetal (FEMA GRAS[1] 3807), Menthone Glyceryl Ketal (FEMA GRAS 3808), Menthyl Lactate (FEMA GRAS 3748), Menthol Ethylene Glycol Carbonate (FEMA GRAS 3805), Menthol Propylene Glycol Carbonate (FEMA GRAS 3806), Menthyl-N-ethyloxamate, Monomethyl Succinate (FEMA GRAS 3810), Monomethyl Glutamate (FEMA GRAS 4006), Menthoxy-1,2-propanediol (FEMA GRAS 3784), Menthoxy-2-methyl-1,2-propanediol (FEMA GRAS 3849), and also the menthane carboxylic acid esters and amides WS-3, WS-4, WS-5, WS-12, WS-14 and WS-30, and mixtures thereof.

[1] FEMA stands for "Flavor and Extract Manufacturers Association" and GRAS is defined as "Generally Regarded As Safe". A FEMA GRAS designation means that the substance thus labelled is tested according to standard method and is considered to be toxicologically safe.

A first important representative of these substances is Monomenthyl Succinate (FEMA GRAS 3810). Both the succinate and the analogous Monomenthyl Glutarate (FEMA GRAS 4006) are important representatives of monomenthyl esters based on di- and polycarboxylic acids:

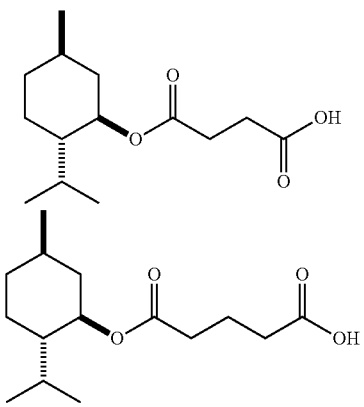

Examples of applications of the substances can be found for example in the documents WO 2003 043431 (Unilever) or EP 1332772 A1 (IFF).

The next important group of menthol compounds preferred in the context of the invention includes carbonate esters of menthol and polyols, such as, for example, glycols, glycerol or carbohydrates, such as, for example, menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Preference is likewise given to the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA. Among these substances, menthone glyceryl acetal/ketal and menthyl lactate and also menthol ethylene glycol carbonate and menthol propylene glycol carbonate, which the applicant sells under the names Frescolat® MGA, Frescolat® ML, Frescolat® MGC and Frescolat® MPC, have proven to be very particularly advantageous.

In the 1970s, menthol compounds were developed for the first time which have a C—C bond in the 3 position and from which likewise a series of representatives can be used. These substances are generally referred to as WS grades. The basic body is a menthol derivative in which the hydroxyl group is exchanged for a carboxyl group (WS-1). All other WS grades are derived from this structure, such as for example the preferred species WS-3, WS-4, WS-5, WS-12, WS-14 and WS-30.

Consistency Regulators and Thickeners

Suitable consistency regulators are primarily fatty alcohols or hydroxy fatty alcohols having 12 to 22 and preferably 16 to 18 carbon atoms and in addition partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are for example Aerosil grades (hydrophilic silicas), polysaccharides, in particular xanthan gum, guar guar, agar agar, alginates and tyloses, carboxymethyl cellulose and hydroxyethyl- and hydroxypropylcellulose, also higher molecular weight polyethylene glycol mono- and diesters of fatty acids, polyacrylates, (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as e.g. Bentone® Gel VS-5PC (Rheox), which is a mixture of cyclopentasiloxane, disteardimonium hectorite and propylene carbonate, have also proven to be particularly effective. Also of suitability are surfactants, such as, for example, ethoxylated fatty acid glycerides, esters of fatty acids with polyols such as, for example, pentaerythritol or trimethylolpropane, fatty alcohol ethoxylates with a narrowed homologue distribution or alkyl oligoglucosides, and also electrolytes such as sodium chloride and ammonium chloride.

Superfatting Agents and Stabilizers

Superfatting agents that can be used are substances such as, for example, lanolin and lecithin, and also polyethoxylated or acylated lanolin and lecithin derivatives, polyol fatty acid esters, monoglycerides and fatty acid alkanolamides, with the latter simultaneously serving as foam stabilizers.

Stabilizers that can be used are metal salts of fatty acids, such as e.g. magnesium, aluminium and/or zinc stearates and ricinoleates.

Polymers

Suitable cationic polymers are, for example, cationic cellulose derivatives, such as e.g. a quaternized hydroxyethylcellulose, which is available under the name Polymer JR 400® from Amerchol, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides, such as, for example, lauryldimonium hydroxypropyl hydrolyzed collagen (Lamequat®L/Grunau), quaternized wheat polypeptides, polyethyleneimine, cationic silicone polymers, such as e.g. amodimethicones, copolymers of adipic acid and dimethylaminohydroxypropyl diethylene triamine (Cartaretine®/Sandoz), copolymers of acrylic acid with dimethyldiallylammonium chloride (Merquat® 550/Chemviron), polyaminopolyamides, and crosslinked water-soluble polymers thereof, cationic chitin derivatives such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, such as e.g. Jaguar® CBS, Jaguar® C-17, Jaguar® C-16 from Celanese, quaternized ammonium salt polymers, such as e.g. Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl trimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Silicone Compounds

Suitable silicone compounds are, for example, dimethylpolysiloxanes, methylphenylpolysiloxanes, cyclic silicones, and also amino-, fatty-acid-, alcohol-, polyether-, epoxy-, fluorine-, glycoside- and/or alkyl-modified silicone compounds, which can be present at room temperature either as a liquid or else in resin form. Also of suitability are simethicones, which are mixtures of dimethicones with an average chain length of from 200 to 300 dimethylsiloxane units and hydrogenated silicates.

UV Light Protection Factors

UV light protection factors are to be understood as meaning for example organic substances (light protection filters) that are present in liquid or crystalline form at room temperature and which are able to absorb ultraviolet rays and release the absorbed energy again in the form of longer-wave radiation, e.g. heat. Usually, the UV light protection factors are present in amounts of from 0.1 to 5 and preferably 0.2 to 1% by weight. UVB filters can be oil-soluble or water-soluble. Examples of oil-soluble substances are:

3-benzylidenecamphor or 3-benzylidenenorcamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, such as e.g. 2,4,6-trianilino(p-carbo-2'-ethyl-1'-hexyloxy)-1,3,5-triazine and octyl triazone or dioctyl butamido triazone (Uvasorb® HEB);

propane-1,3-diones, such as e.g. 1-(4-tert-butylphenyl)-3-(4'-methoxyphenyl)propane-1,3-dione;

ketotricyclo(5.2.1.0)decane derivatives.

Suitable water-soluble substances are:

2-phenylbenzimidazole-5-sulphonic acid and the alkali metal, alkaline earth metal, ammonium, alkylammonium, alkanolammonium and glucammonium salts thereof;

1H-benzimidazole-4,6-disulphonic acid, 2,2'-(1,4-phenylene)bis-, disodium salt (Neo Heliopan® AP)

sulphonic acid derivatives of benzophenones, preferably 2-hydroxy-4-methoxybenzophenone-5-sulphonic acid and its salts;

sulphonic acid derivatives of 3-benzylidenecamphor, such as e.g. 4-(2-oxo-3-bornylidene methyl)benzene sulphonic acid and 2-methyl-5-(2-oxo-3-bornylidene)sulphonic acid and salts thereof.

Suitable typical UV-A filters are in particular derivatives of benzoylmethane, such as for example 1-(4'-tert-butylphenyl)-3-(4'-methoxyphenyl)propane-1,3-dione, 4-tert-butyl-4'-methoxydibenzoylmethane (Parsol® 1789), 2-(4-diethylamino-2-hydroxybenzoyl)benzoic acid hexyl ester (Uvinul® A Plus), 1-phenyl-3-(4'-isopropylphenyl)propane-1,3-dione, and enamine compounds. The UV-A and UV-B filters can of course also be used in mixtures. Particularly favourable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Such combinations are advantageously combined with water-soluble filters such as e.g. 2-phenylbenzimidazole-5-sulphonic acid and the alkali metal, alkaline earth metal, ammonium, alkylammonium, alkanolammonium and glucammonium salts thereof.

Besides the stated soluble substances, insoluble light protection pigments, namely finely disperse metal oxides and salts are also suitable for this purpose. Examples of suitable metal oxides are in particular zinc oxide and titanium dioxide and in addition oxides of iron, zirconium, silicon, manganese, aluminium and cerium, and mixtures thereof. Salts that can be used are silicates (talc), barium sulphate and zinc stearate. The oxides and salts are used in the form of the pigments for skincare and skin-protecting emulsions and decorative cosmetics. The particles here should have an average diameter of less than 100 nm, preferably between 5 and 50 nm and in particular between 15 and 30 nm. They can have a spherical shape, although it is also possible to use those particles which have an ellipsoidal shape or a shape which deviates in some other way from the spherical configuration. The pigments can also be present in surface-treated form, i.e. hydrophilicized or hydrophobicized. Typical examples are coated titanium dioxides, such as e.g. titanium dioxide T 805 (Degussa) or Eusolex® T2000, Eusolex® T, Eusolex® T-ECO, Eusolex® T-S, Eusolex® T-Aqua, Eusolex® T-45D (all Merck), Uvinul $TiO_2$ (BASF). Suitable hydrophobic coating agents here are in particular silicones and specifically trialkoxyoctylsilanes or simethicones. In sun protection compositions, preference is given to using so-called micro- or nanopigments. Preference is given to using micronized zinc oxide such as e.g. Z-COTE® or Z-COTE HP1®.

Humectants

Humectants serve to further optimize the sensory properties of the composition and for regulating the moisture in the skin. At the same time, the low-temperature stability of the preparations according to the invention is increased, especially in the case of emulsions. The humectants are usually present in an amount of from 0.1 to 15% by weight, preferably 1 to 10% by weight, and in particular 5 to 10% by weight.

Of suitability according to the invention are, inter alia, amino acids, pyrrolidone carboxylic acid, lactic acid and salts thereof, lactitol, urea and urea derivatives, uric acid, glucosamine, creatinine, cleavage products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (including fructose, glucose, maltose, maltitol, mannitol, inositol, sorbitol, sorbitylsilanediol, sucrose, trehalose, xylose, xylitol, glucuronic acid and salts thereof), ethoxylated sorbitol (sorbeth-6, sorbeth-20, sorbeth-30, sorbeth-40), honey and hydrogenated honey, hydrogenated starch hydrolysates, and mixtures of hydrogenated wheat protein and PEG-20 acetate copolymer. According to the invention, glycerol, diglycerol, triglycerol and butylene glycol are preferably suitable as humectants.

Biogenic Active Ingredient and Antioxidants

Biogenic active ingredients are for example to be understood as meaning tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as e.g. prune extract, bambaranut extract and vitamin complexes.

Antioxidants interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocaninic acid) and derivatives thereof, peptides such as D,L-carnosine, D-carnosine, L-carnosine and derivatives thereof (e.g. anserine), carotenoides, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthioninesulphones, penta-, hexa-, heptathionine sulphoximine) in very low tolerated doses (e.g. pmol to µmol/kg), also (metal) chelating agents (e.g. α-hydroxy fatty acids, palmitic acid, phytinic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferrulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these specified active ingredients that are suitable according to the invention.

Deodorants and Germicidal Agents

Cosmetic deodorants counteract, conceal or eliminate body odours. Body odours are formed as a result of the action of skin bacteria on apocrine perspiration, during which unpleasant-smelling degradation products are formed. Accordingly, deodorants comprise active ingredients which function as germicidal agents, enzyme inhibitors, odour absorbers or odour concealers.

Germicidal agents. Suitable germicidal agents are in principle all substances effective against Gram-positive bacteria, such as e.g. 4-hydroxybenzoic acid and its salts and esters, N-(4-chlorophenyl)-N"-(3,4-dichlorophenyl)urea, 2,4,4"-trichloro-2"-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DMC), salicylic acid N-alkylamides such as e.g. salicylic acid n-octylamide or salicylic acid n-decylamide.

Enzyme inhibitors. Suitable enzyme inhibitors are, for example, esterase inhibitors. These are preferably trialkyl citrates such as trimethyl citrate, tripropyl citrate, triisopropyl citrate, tributyl citrate and in particular triethyl citrate (Hydagen® CAT). The substances inhibit the enzyme activity and thereby reduce the odour formation. Further substances which are contemplated as esterase inhibitors are sterol sulphates or phosphates, such as, for example, lanosterol, cholesterol, campesterol, stigmasterol and sitosterol sulphates or phosphates, dicarboxylic acids and esters thereof, such as, for example, glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, such as, for example, citric acid, malic acid, tartaric acid or tartaric acid diethyl ester, and also zinc glycinate.

Odour absorbers. Substances suitable as odour absorbers are those which are able to absorb and largely retain odour-forming compounds. They reduce the partial pressure of the individual components and thus also reduce their spreading rate. It is important here that perfumes must remain unaffected. Odour absorbers have no effectiveness towards bacteria. They contain for example as the main constituent a complex zinc salt of ricinoleic acid or specific, largely odour-neutral fragrances, which are known to the person skilled in the art as "fixatives", such as e.g. extracts of labdanum or styrax or certain abietic acid derivatives. Functioning as odour concealers are fragrances or perfume oils which, in addition to their function as odour concealers, impart their particular scent note to the deodorants. Perfume oils that may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also of suitability are animal raw materials, such as, for example, civet and castoreum. Typical synthetic fragrance compounds are products of the ester, ether, aldehyde, ketone, alcohol and hydrocarbon types. Fragrance compounds of the ester type are e.g. benzyl acetate, p-tert-butyl cyclohexylacetate, linalyl acetate, phenylethyl acetate, linalyl benzoate, benzyl formate, allyl cyclohexylpropionate, styrallyl propionate and benzyl salicylate. The ethers include, for example, benzyl ethyl ether, the aldehydes include e.g. the linear alkanals having 8 to 18 carbon atoms, citral, citronellal, citronellyloxyacetaldehyde, cyclamenaldehyde, hydroxycitronellal, lilial and bourgeonal; the ketones include e.g. the ionones and methyl cedryl ketone; the alcohols include anethol, citronellol, eugenol, isoeugenol, geraniol, linalool, phenylethyl alcohol and terpineol; the hydrocarbons include primarily the terpenes and balsams. However, preference is given to using mixtures of different fragrances which together produce a pleasant scent note. Essential oils of lower volatility, which are mostly used as aroma components, are also suitable as perfume oils, e.g. sage oil, camomile oil, clove oil, melissa oil, mint oil, cinnamon leaf oil, linden blossom oil, juniper berry oil, vetiver oil, olibanum oil, galbanum oil, labdanum oil and lavandin oil. Preferably, bergamot oil, dihydromyrcenol, lilial, lyral, citronellol, phenylethyl alcohol, α-hexyl-cinnamaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat alone or in mixtures, are used.

Antiperspirants. Antiperspirants reduce the formation of perspiration by influencing the activity of the eccrine sweat glands, and thus counteract armpit wetness and body odour. Aqueous or anhydrous formulations of antiperspirants typically comprise the following ingredients:
astringent active ingredients,
oil components,
nonionic emulsifiers,
coemulsifiers,
consistency regulators,
auxiliaries such as e.g. thickeners or complexing agents and/or
nonaqueous solvents such as e.g. ethanol, propylene glycol and/or glycerol.

Suitable astringent antiperspirant active ingredients are in particular salts of aluminium, zirconium or zinc. Such suitable antihydrotically effective substances are e.g. aluminium chloride, aluminium chlorohydrate, aluminium dichlorohydrate, aluminium sesquichlorohydrate and complex compounds thereof e.g. with propylene glycol-1,2. Aluminium hydroxyallantoinate, aluminium chloride tartrate, aluminium zirconium trichlorohydrate, aluminium zirconium tetrachlorohydrate, aluminium zirconium pentachlorohydrate and complex compounds thereof e.g. with amino acids such as glycine. In addition, oil-soluble and water-soluble auxiliaries customary in antiperspirants may be present in relatively small amounts. Such oil-soluble auxiliaries can be for example:
antiflammatory, skin-protecting or nice-smelling essential oils,
synthetic skin-protecting active ingredients and/or
oil-soluble perfume oils.

Customary water-soluble additives are e.g. preservatives, water-soluble fragrances, pH regulators, e.g. buffer mixtures, water-soluble thickeners, e.g. water-soluble natural or synthetic polymers such as e.g. xanthan gum, hydroxyethyl cellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazol®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulphide, sulphur colloidal, sulphur polyethylene glycol sorbitan monooleate, sulphur ricinol polyethoxylate, sulphur tar distillates, salicylic acid (or in combination with hexachlorophene), undecylenic acid monoethanolamide sulphosuccinate Na salt, Lamepon® UD (protein-undecylenic acid condensate), zinc pyrithione, aluminium pyrithione and magnesium pyrithione/dipyrithione magnesium sulphate.

Swelling Agents

Swelling agents used for aqueous phases can be montmorillonites, clay mineral substances, pemulen, and alkyl-modified carbopol grades (Goodrich). Further suitable polymers and swelling agents can be found in the overview by R. Lochhead in *Cosm. Toil.* 108, 95 (1993).

Insect Repellents

Suitable insect repellents are N,N-diethyl-m-toluamide, 1,2-pentanediol or ethyl butylacetylaminopropionate. A suitable self-tanning agent is dihydroxyacetone. Suitable as tyrosine inhibitors, which prevent the formation of melanine and are used in depigmentation compositions, are, for example, arbutin, ferrulic acid, kojic acid, coumaric acid and ascorbic acid (vitamin C).

Ingredients for Oral and Dental Care Compositions

Toothpastes or dental creams are generally understood as being gel-like or pasty preparations made of water, thickeners, humectants, abrasive or polishing bodies, surfactants, sweeteners, aroma substances, deodorizing active ingredients and active ingredients to combat oral and dental diseases. In the toothpastes according to the invention it is possible to use all customary cleaning bodies, such as e.g. chalk, dicalcium phosphate, insoluble sodium metaphosphate, aluminium silicates, calcium pyrophosphate, finely divided synthetic resins, silicas, aluminium oxide and aluminium oxide trihydrate.

Preferably suitable cleaning bodies for the toothpastes according to the invention are in particular finely divided xerogel silicas, hydrogel silicas, precipitated silicas, aluminium oxide trihydrate and finely divided alpha-aluminium oxide or mixtures of these cleaning bodies in amounts of from 15 to 40% by weight of the toothpaste. Suitable humectants are predominantly low molecular weight polyethylene glycols, glycerol, sorbitol or mixtures of these products in amounts up to 50% by weight. Among the known thickeners, the thickening, finely divided gel silicas and hydrocolloids, such as e.g. carboxymethylcellulose, hydroxyethylcellulose, hydroxypropylguar, hydroxyethyl starch, polyvinylpyrrolidone, high molecular weight polyethylene glycol, plant gums such as tragacanth, agar agar, carrageen moss, gum arabic, xantham gum and carboxyvinyl polymers (e.g. Carbopol® grades) are suitable. In addition to the mixtures of menthofuran and menthol compounds, the oral and dentalcare compositions can comprise in particular surface-active substances, preferably anionic and nonionic high-foam surfactants, such as the substances already specified above, but in particular alkyl ether sulphate salts, alkyl polyglucosides and mixtures thereof.

Further customary toothpaste additives are:
preservatives and antimicrobial substances such as e.g. p-hydroxybenzoic acid methyl, ethyl or propyl ester, sodium sorbate, sodium benzoate, bromochlorophene, phenyl salicylic acid ester, thymol and the like;
anti-tartar active ingredients, e.g. organophosphates such as 1-hydroxyethane-1,1-diphosphonic acid, 1-phosphonopropane-1,2,3-tricarboxylic acid and others which are known e.g. from U.S. Pat. No. 3,488,419, DE 2224430 A1 and DE 2343196 A1;
other caries-inhibiting substances such as e.g. sodium fluoride, sodium monofluorophosphate, tin fluoride;
sweeteners, such as e.g. saccharin sodium, sodium cyclamate, sucrose, lactose, maltose, fructose or Apartam®, (L-aspartyl-L-phenylalanine methyl ester), stevia extracts or sweetening constituents thereof, in particular rebaudioside;
additional aromas such as e.g. eucalyptus oil, anise oil, fennel oil, caraway oil, methyl acetate, cinnamaldehyde, anethole, vanillin, thymol, and mixtures of these and other natural and synthetic aromas;
pigments such as e.g. titanium dioxide;
dyes;
buffer substances such as e.g. primary, secondary or tertiary alkali metal phosphates or citric acid/sodium citrate;
wound-healing and inflammatory substances such as e.g. allantoin, urea, azulene, chamomile active ingredients and acetyl salicylic acid derivatives.

A preferred embodiment of the cosmetic preparations is toothpastes in the form of an aqueous, pasty dispersion, comprising polishing agents, humectants, viscosity regulators and optionally further customary components, and also the mixture of menthofuran and menthol compounds in amounts of from 0.5 to 2% by weight.

In mouthwashes, a combination with aqueous-alcoholic solutions of varying concentration gradient of essential oils, emulsifiers, astringent and toning drug extracts, tartar-inhibiting, antibacterial additives and taste correctors is directly possible. A further preferred embodiment of the invention is a mouthwash in the form of an aqueous or aqueous-alcoholic solution comprising the mixture of menthofuran and menthol compounds in amounts of from 0.5 to 2% by weight. In mouthwashes which are diluted prior to use, adequate effects can be attained using higher concentrations corresponding to the intended dilution ratio.

Hydrotropes

To improve the flow behaviour, hydrotropes, such as, for example ethanol, isopropyl alcohol, or polyols can also be used; these substances largely correspond to the carriers described at the start. Polyols that are contemplated here have preferably 2 to 15 carbon atoms and at least two hydroxyl groups. The polyols can also contain further functional groups, in particular amino groups, and/or be modified with nitrogen. Typical examples are
glycerol;
alkylene glycols, such as, for example, ethylene glycol, diethylene glycol, propylene glycol, butylene glycol, hexylene glycol, and polyethylene glycols with an average molecular weight of from 100 to 1000 Daltons;
technical oligoglycerol mixtures with a degree of self-condensation of from 1.5 to 10, such as for example technical-grade diglycerol mixtures with a diglycerol content of from 40 to 50% by weight;
methylol compounds, such as in particular trimethylolethane, trimethylolpropane, trimethylolbutane, pentaerythritol and dipentaerythritol;
low alkyl glucosides, in particular those having 1 to 8 carbon atoms in the alkyl radical, such as, for example, methyl- and butylglucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcoholamines, such as diethanolamine or 2-amino-1,3-propanediol.

Preservatives

Suitable preservatives are, for example, phenoxyethanol, formaldehyde solution, parabens, pentanediol or sorbic acid, as well as the silver complexes known under the name Surfacine® and the other classes of substance listed in Annex 6, part A and B of the Cosmetics Ordinance.

Perfume Oils and Aromas

Perfume oils that may be mentioned are mixtures of natural and synthetic fragrances. Natural fragrances are extracts of flowers (lily, lavender, rose, jasmine, neroli, ylang-ylang), stems and leaves (geranium, patchouli, petitgrain), fruits (anise, coriander, caraway, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also of suitability are animal raw materials such as, for example, civet and castoreum. Typical synthetic fragrance compounds are products of the ester, ether, aldehyde, ketone, alcohol and hydrocarbon types. Fragrance compounds of the ester type are e.g. benzyl acetate, phenoxyethyl isobutyrate, p-tert-butylcyclohexyl acetate, linalyl acetate, dimethylbenzyl carbinylacetate, phenylethyl acetate, linalyl benzoate, benzyl formate, ethyl methylphenyl glycinate, allyl cyclohexylpropionate, styrallyl propionate and benzyl salicylate. The ethers include, for example, benzyl ethyl ether; the aldehydes include e.g. the linear alkanals having 8 to 18 carbon atoms, citral, citronellal, citronellyloxyacetaldehyde, cyclamenaldehyde, hydroxycitronellal, lilial and bourgeonal; the ketones include e.g. the ionones, α-isomethylionone and methyl cedryl ketone; the alcohols include anethole, citronellol, eugenol, isoeugenol, geraniol, linalool, phenylethyl alcohol and terpineol; the hydrocarbons include primarily the terpenes and balsams. However, preference is given to using mixtures of different fragrances which together produce a pleasant scent note. Essential oils of lower volatility, which are mostly used as aroma components, are also suitable as perfume oils, e.g. sage oil, chamomile oil, clove oil, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, Boisambrene Forte, ambroxan, indole, hedione, sandelice, lemon oil, mandarin oil, orange oil, allyl amylglycolate, cyclovertal, lavandin oil, clary sage oil, β-damascone, geranium oil bourbon, cyclohexyl salicylate, Vertofix Coeur, Iso-E-Super, Fixolide NP, evernyl, iraldein gamma, phenyl acetic acid, geranyl acetate, benzyl acetate, rose oxide, romillat, irotyl and floramat, alone or in mixtures.

Suitable aromas are, for example, peppermint oil, spearmint oil, aniseed oil, star anise oil, caraway oil, eucalyptus oil, fennel oil, lemon oil, wintergreen oil, clove oil, menthol and the like.

Dyes

Dyes which can be used are the substances approved and suitable for cosmetic purposes, as are listed for example in the publication "Kosmetische Färbemittel [Cosmetic Colorants]" of the Farbstoffkommission der Deutschen Forschungsgemeinschaft [Dyes Commission of the German Research Society], Verlag Chemie, Weinheim, 1984, pp. 81-106. Examples are cochenille red A (C.I.16255), patent blue V (C.I.42051), indigotin (C.I.73015), chlorphyllin (C.I.75810), quinoline yellow (C.I.47005), titanium dioxide (C.I.77891), indanthrene blue RS (C.I.69800) and madder lake (C.I.58000). Luminol may also be present as luminescence dye. These dyes are usually used in concentrations of from 0.001 to 0.1% by weight, based on the total mixture.

The total fraction of auxiliaries and additives can be 1 to 50, preferably 5 to 40, % by weight—based on the compositions. The compositions can be produced by customary cold or hot processes; preference is given to working in accordance with the phase inversion temperature method.

Mixtures

A further subject matter of the invention relates to a first mixture of at least four lactones selected from the group consisting of γ-hexalactone, γ-heptalactone, γ-octalactone, γ-nonalactone, γ-decalactone, γ-undecalactone, γ-dodecalactone, δ-hexalactone, δ-heptalactone, δ-octalactone, δ-nonalactone, δ-decalactone, δ-undecalactone, δ-dodecalactone.

This is because it has been proven that the best odiferous improvements can be attained if more than one of the lactones to be used according to the invention, preferably two and in particular three or four lactones, are used together, where the weight ratio should be approximately balanced.

In a first preferred embodiment of the invention, either only γ-lactones or only δ-lactones are used. In a second, the lactone mixtures to be used in each case comprise γ- and δ-lactones of identical chain length. Particularly preferred mixtures comprise in each case γ-decalactone and γ-undecalactone.

The mixtures can be added to the end products in the amounts already stated, e.g. 0.01 to 1% by weight, in particular 0.02 to 0.5% by weight and particularly preferably 0.05 to 0.1% by weight—based on the preparations.

A further subject matter of the invention is directed to a second mixture comprising (a) at least two representatives of the group which is formed by nonalactone, decalactone and undecalactone, and also
(b) aldehydes of the formula (II)

$$R^2COH \qquad (II)$$

in which $R^2$ is a linear or branched, saturated or unsaturated alkyl and/or alkenyl radical having 6 to 22 carbon atoms.

Preferably, the mixtures according to the invention comprise, as component (a), gamma-lactones and, as component (b) unsaturated aldehydes which are preferably present in trans-conformation and in particular have 8 to 12 carbon atoms. The mixtures comprise the components (a) and (b) preferably in quantitative ratios of from 1:0.00001 to 1:120, preferably 1:0.001 to 1:50, in particular 1:0.01 to 1:10 and particularly preferably 1:0.1 to 1:1.

The mixtures according to the invention are characterized in that they are characterized by an intense milky-creamy odour whereas the lactones per se are virtually odour-less and the aldehydes have a pungent, greasy and extremely unpleasant odour.

EXAMPLES

Examples 1 and 2, Comparative Example C1

A commercially available soap base (Soap Base VVF, Henkel Poland) was admixed with in each case 0.05% by weight of a mixture (a) of γ-decalactone and γ-undecalactone (weight ratio 1:1) and (b) γ-nonalactone, γ-decalactone, δ-decalactone and γ-undecalactone (weight ratio 1:1:1:1) and the odour sensorics by a panel consisting of 5. Intensity scale from 1 to 25. The results are summarized in Table 1. Examples 1 and 2 are in accordance with the invention, example C1 serves for comparison.

TABLE 1

Sensory assessment of a soap base

| Odour note | C1 | 1 | 2 |
|---|---|---|---|
| Positive odour notes | | | |
| sweet | 1 | 17 | 18 |
| creamy | 4 | 13 | 12 |
| floral | 1 | 2 | 2 |
| aromatic | 2 | 1 | 1 |
| Negative odour notes | | | |
| greasy | 4 | 1 | 1 |
| oxidized | 11 | 2 | 2 |
| chemical | 2 | 2 | 2 |
| musty | 1 | 1 | 1 |

The examples and the comparative example show that by adding even small amounts of lactones not only are the negative odour notes of the soap mixture masked, but instead pleasant odour notes come to the fore.

Formulation examples for various laundry detergents, dishwashing detergents and cleaners which comprise the lactones to be used according to the invention are given below. As the product NeoScent AA, a mixture of γ-nonalactone, γ-decalactone, δ-decalactone and γ-undecalactone (weight ratio 1:1:1:1) is used. All quantitative amounts are % by weight.

TABLE 2

Bar soaps

| Composition | A1 | A2 | A3 |
|---|---|---|---|
| Sodium C12/14 Olefin Sulphonate | 40.0 | — | — |
| Disodium Lauryl Sulphosuccinate | — | 40.0 | — |
| Lauryl Glucoside | 15.0 | 15.0 | 55.0 |
| Cetylstearyl Alcohol | 12.0 | 12.0 | 12.0 |
| Paraffin Oil (m.p. 54 to 56° C.) | 8.0 | 8.0 | 8.0 |
| Maize Starch, degraded | 8.0 | 8.0 | 8.0 |
| Palmitic Acid (and) Stearic Acid | 5.5 | 5.5 | 5.5 |
| Glyceryl Stearate | 2.0 | 2.0 | 2.0 |
| Coco Glyceride | 2.0 | 2.0 | 2.0 |
| Polyquaternium-7 | 1.0 | 1.0 | 1.0 |
| Perfume oil | 1.0 | 1.0 | 1.0 |
| Titanium dioxide | 0.5 | 0.5 | 0.5 |
| NeoScent AA | 0.05 | 0.05 | 0.05 |
| Water | ad 100 | | |

TABLE 3

Syndet soaps

| Composition | B1 | B2 | B3 |
|---|---|---|---|
| Lauryl Glucoside | 15.0 | 15.0 | 15.0 |
| Sodium C12/14 Olefin Sulphonate | 40.0 | 40.0 | — |
| Sodium Lauryl Sulphate | — | — | 40.0 |
| Paraffin Oil (m.p. 54° C.) | 8.0 | 8.0 | 8.0 |
| Tallow Fatty Alcohol | 7.0 | 7.0 | 7.0 |
| Maize starch | 17.0 | — | 17.0 |
| Dextrose | — | 17.0 | — |
| Coco Fatty Acids | 10.0 | 10.0 | 10.0 |
| Titanium dioxide | 1.0 | 1.0 | 1.0 |
| Perfume oil | 1.0 | 1.0 | 1.0 |
| NeoScent AA | 0.05 | 0.05 | 0.05 |
| Water | ad 100 | | |

TABLE 4

WC gel toilet blocks

| Composition | C1 | C2 | C3 | C4 | C5 | C6 |
|---|---|---|---|---|---|---|
| Lauryl Glucoside | 5.0 | 1.5 | 1.5 | 1.5 | 5.0 | 1.5 |
| Decyl Glucoside | — | 3.5 | 3.5 | 3.5 | — | 3.5 |
| Sodium Lauryl Sulphate | 9.0 | 6.0 | 3.0 | — | 9.0 | 6.0 |
| Sodium Laureth Sulphate | — | 3.0 | — | — | — | 3.0 |
| Cocamidopropyl Betaine | — | — | 6.0 | 9.0 | — | — |
| Ethanol | 3.5 | 3.5 | 3.5 | 3.5 | 3.5 | 3.5 |
| Citric Acid Mono Hydrate | 3.6 | 3.6 | 3.6 | 3.6 | 3.6 | 3.6 |
| Sodium Hydroxide | 0.5 | 0.5 | 0.5 | 0.5 | 0.5 | 0.5 |
| Laurylamine + 1EO | 4.5 | 3.0 | 5.0 | 2.5 | — | — |
| Hexanediol-1,6 | — | 0.5 | — | — | 0.5 | — |
| Perfume oil | 0.5 | 0.5 | 0.5 | 0.5 | 0.5 | 0.5 |
| NeoScent AA | 0.05 | 0.05 | 0.05 | 0.05 | 0.05 | 0.05 |
| Water | ad 100 | | | | | |

TABLE 5

Bleach solutions

| Composition | D1 | D2 | D3 | D4 | D5 |
|---|---|---|---|---|---|
| Sodium hypochlorite | 4.0 | 4.0 | 4.0 | 4.0 | 4.0 |
| Sodium hydroxide | 0.9 | 0.9 | 0.9 | 0.9 | 0.9 |
| Sodium Laureth-2 Sulphate | — | 2.0 | 2.0 | — | 2.0 |
| Lauryldimethylamine oxide | — | 2.0 | — | — | 2.0 |
| Coco Glucosides | — | — | 0.5 | — | — |
| Laureth-2 | — | — | 1.0 | — | — |
| Sodium silicate | 0.95 | 0.95 | 0.95 | 0.95 | 0.95 |
| Sodium carbonate | — | — | — | — | — |
| Amine oxide phosphonic acid | 0.1 | 0.1 | 0.1 | 0.1 | 0.1 |
| Polyacrylate | 1.0 | 1.0 | 1.0 | 1.0 | 1.0 |
| Perfume oil | 0.5 | 0.5 | 0.5 | 0.5 | 0.5 |
| NeoScent AA | 0.05 | 0.05 | 0.05 | 0.05 | 0.05 |
| Water | ad 100 | | | | |

TABLE 6

Powder detergents

| Composition | E1 | E2 | E3 | E4 | E5 | E6 |
|---|---|---|---|---|---|---|
| Sodium Laureth-1 Sulphate | 12.0 | 8.0 | 8.0 | 4.0 | 4.0 | — |
| Dodecylbenzene sulphonate | — | — | 4.0 | 8.0 | 4.0 | 8.0 |
| Sodium Lauryl Sulphate | — | 4.0 | — | — | 4.0 | 4.0 |
| Coco Fatty Acid, Sodium Salt | 1.0 | 1.0 | 1.0 | 1.0 | 1.0 | 1.0 |
| Coco Glucosides | — | — | — | 7.0 | — | — |
| Laureth-5 | 7.0 | 7.0 | 7.0 | — | 7.0 | 7.0 |
| Zeolite A | 24.0 | 24.0 | 24.0 | 24.0 | 24.0 | 24.0 |
| Sodium silicate, amorphous (modulus 1:2) | 3.0 | 3.0 | 3.0 | 3.0 | 3.0 | 3.0 |
| Sodium carbonate | 12.0 | 12.0 | 12.0 | 12.0 | 12.0 | 12.0 |
| Polymeric polycarboxylate | 5.5 | 5.5 | 5.5 | 5.5 | 5.5 | 5.5 |
| Perborate monohydrate | 16.0 | 16.0 | 16.0 | 16.0 | 16.0 | 16.0 |
| Tetraacetylethylenediamine | 5.5 | 5.5 | 5.5 | 5.5 | 5.5 | 5.5 |
| Carboxymethylcellulose | 0.3 | 0.3 | 0.3 | 0.3 | 0.3 | 0.3 |
| Optical brightener | 0.2 | 0.2 | 0.2 | 0.2 | 0.2 | 0.2 |
| Enzyme granules (protease) | 1.0 | 1.0 | 1.0 | 1.0 | 1.0 | 1.0 |
| Perfume oil | 0.5 | 0.5 | 0.5 | 0.5 | 0.5 | 0.5 |
| NeoScent AA | 0.05 | 0.05 | 0.05 | 0.05 | 0.05 | 0.05 |
| Water | ad 100 | | | | | |

TABLE 7

Hand dishwashing detergent

| Composition | F1 | F2 | F3 | F4 |
|---|---|---|---|---|
| Sodium Laureth-1 Sulphate | 15 | 15 | 15 | 15 |
| Sodium Laureth-2 Sulphate | 15 | — | — | — |
| Sodium Lauryl Sulphate | — | 15 | — | — |

TABLE 7-continued

Hand dishwashing detergent

| Composition | F1 | F2 | F3 | F4 |
|---|---|---|---|---|
| Coco Glucosides | — | — | 15 | — |
| Sodium Octyl Sulphosuccinate | — | — | — | 15 |
| Cocamidopropyl Betaine | 1 | 3 | 3 | 3 |
| Perfume oil | 0.5 | 0.5 | 0.5 | 0.5 |
| NeoScent AA | 0.05 | 0.05 | 0.05 | 0.05 |
| Water | ad 100 | | | |

TABLE 8

Cleaner

| Composition | G1 | G2 | G3 | G4 | G5 | G6 |
|---|---|---|---|---|---|---|
| $C_{12/16}$-Alkyl sulphate Na salt | 5.0 | 5.0 | 4.0 | 0 | 5.0 | 0 |
| $C_{16/18}$-Tallow fatty alcohol + 25EO | 3.0 | 3.0 | 4.0 | 0 | 0 | 5.0 |
| $C_{12/14}$-Cocoalkyl oligoglucoside | 1.0 | 2.0 | 2.0 | 5.0 | 0 | 0 |
| Sodium metasilicate | 15.0 | 15.0 | 15.0 | 15.0 | 15.0 | 15.0 |
| Sodium carbonate | 26.0 | 24.0 | 24.0 | 30.0 | 30.0 | 30.0 |
| Sulphonated styrene/MSA copolymer, sodium salt | — | 2.0 | 2.0 | — | — | — |
| Limonene | 0.1 | 0.1 | 0.1 | 0.1 | 0.1 | 0.1 |
| NeoScent AA | 0.05 | 0.05 | 0.05 | 0.05 | 0.05 | 0.05 |
| Sodium tripolyphosphate | ad 100 | | | | | |

TABLE 9

Cosmetic cream

| Composition | H1 | H2 | H3 | H4 | H5 |
|---|---|---|---|---|---|
| Glyceryl Stearate (and) Ceteareth 12/20 (and) Cetearyl Alcohol (and) Cetyl Palmitate | 5.0 | 5.0 | 4.0 | — | — |
| Ceteareth-12 | — | — | 1.0 | — | — |
| Polyglyceryl-3 Isostearate | — | — | — | 4.0 | — |
| Polyglyceryl-2 Dipolyhydroxystearate | — | — | — | — | 4.0 |
| Glyceryl Oleate | — | — | — | 2.0 | — |
| PEG-7 Glyceryl Cocoate | — | — | — | — | 2.0 |
| Dicaprylyl Ether | — | — | — | 5.0 | 6.0 |
| Hexyldecanol (and) Hexyldecyl Laurate | — | — | 3.0 | 10.0 | 9.0 |
| Cetearyl Isononanoate | 3.0 | 3.0 | — | — | — |
| Decyl Oleate | 3.0 | 3.0 | — | — | — |
| Coco Caprylate Caprate | — | — | 3.0 | 5.0 | 5.0 |
| Beeswax | — | — | — | 7.0 | 5.0 |
| Hydrolyzed Elastin | 2.0 | — | — | — | — |
| Hydrolyzed Collagen | — | 2.0 | — | — | — |
| Hydrolyzed Wheat Gluten | — | — | 0.5 | — | — |
| Sodium Cocoyl Hydrolyzed Wheat Protein | — | — | — | 0.5 | 0.5 |
| Glycol Distearate (and) Laureth-4 (and) Cocamidopropyl Betaine | 5.0 | 5.0 | 4.0 | — | — |
| Glycerin (86% strength by weight) | — | — | 1.0 | — | — |
| Perfume oil | 0.5 | 0.5 | 0.5 | 0.5 | 0.5 |
| NeoScent AA | 0.05 | 0.05 | 0.05 | 0.05 | 0.05 |
| Water | | | ad 100 | | |

The invention claimed is:

1. A method for masking an odoriferous incorrect note in an oleochemical composition comprising:
adding to said composition
a mixture of at least two lactones comprising:
(a) γ-decalactone and
(b) γ-undecalactone
in an amount of from about 0.01 to 0.1 wt-% based on the weight of the composition, and wherein said composition is selected from the group consisting of a soap base, a laundry detergent, a dishwashing detergent, a hard surface cleaner, and a cosmetic preparation wherein the cosmetic preparation is a cosmetic selected from the group consisting of a cosmetic cream and/or a cosmetic containing an additive selected from the group consisting of a UV light protection factor, an antiperspirant, an antidandruff agent, an insect repellent, a self-tanning agent, and a depigmentation agent, wherein said composition prior to the addition of said lactones has a greasy or a rancid odour note.

2. The method of claim 1, wherein said composition comprises a component causing said incorrect note selected from the group consisting of a free fatty acid, an aldehyde, and an oxidation product of a fat or oil.

3. The method of claim 1 wherein said mixture of at least two lactones further comprising at least one additional lactone selected from the group consisting of γ-hexalactone, γ-heptalactone, γ-octalactone, γ-nonalactone, γ-dodecalactone, δ-hexalactone, δ-heptalactone, δ-octalactone, δ-nonalactone, δ-decalactone, δ-undecalactone, δ-dodecalactone, and mixtures thereof.

4. The method of claim 1, wherein said mixture of at least two lactones consists of:
(a) γ-decalactone;
(b) γ-undecalactone;
(c) γ-nonalactone; and
(d) δ-decalactone.

* * * * *